(12) United States Patent
Boehringer et al.

(10) Patent No.: US 7,144,742 B2
(45) Date of Patent: *Dec. 5, 2006

(54) QUANTITATIVE LATERAL FLOW ASSAYS AND DEVICES

(75) Inventors: Hans Boehringer, San Diego, CA (US); Gerald Rowley, San Diego, CA (US); Allan D. Pronovost, San Diego, CA (US)

(73) Assignee: Quidel Corporation, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/016,550

(22) Filed: Dec. 17, 2004

(65) Prior Publication Data

US 2005/0170527 A1    Aug. 4, 2005

Related U.S. Application Data

(63) Continuation of application No. 08/812,616, filed on Mar. 6, 1997, now Pat. No. 6,924,153.

(51) Int. Cl.
*G01N 33/558* (2006.01)

(52) U.S. Cl. ............ 436/514; 422/55; 422/56; 422/57; 422/58; 435/7.92; 435/7.93; 435/7.94; 435/7.5; 435/287.1; 435/287.2; 435/287.7; 435/287.9; 435/805; 435/810; 435/969; 435/970; 435/973; 435/975; 436/169; 436/513; 436/518; 436/531; 436/533; 436/534; 436/805; 436/808; 436/810

(58) Field of Classification Search ........... 422/55–58, 422/61; 435/7.92, 7.93, 7.94, 7.5, 287.1, 435/287.2, 287.7, 287.9, 805, 810, 969, 970, 435/973, 975; 436/169, 513, 514, 518, 531, 436/533, 534, 805, 808, 810

See application file for complete search history.

(56) References Cited

U.S. PATENT DOCUMENTS

| | | | |
|---|---|---|---|
| 4,168,146 | A | 9/1979 | Grubb et al. |
| 4,271,140 | A | 6/1981 | Bunting |
| 4,435,504 | A | 3/1984 | Zuk et al. |
| 4,496,654 | A | 1/1985 | Katz et al. |
| 4,517,288 | A | 5/1985 | Giegel et al. |
| 4,740,468 | A | 4/1988 | Weng et al. |

(Continued)

FOREIGN PATENT DOCUMENTS

EP        0 191 640        8/1986

(Continued)

OTHER PUBLICATIONS

Allen et al., Clin. Chem. (1990) 36:1591-1597.

(Continued)

*Primary Examiner*—Christopher L. Chin
(74) *Attorney, Agent, or Firm*—Morrison & Foerster LLP

(57) ABSTRACT

This invention provides solid phase specific binding lateral flow assay methods, devices and kits for quantitating high and low molecular weight analytes. The methods and devices of the invention employ labelled reagents which are either analyte analogs or complementary specific binding pair members for the analyte and a novel arrangement of capture zones comprising immobilized specific binding substances for either the analyte or the labelled reagent to effect bound from unbound labelled reagent as a function of analyte concentration. The capture zones are disposed on a non-bibulous matrix defining a flow path from a sample receiving zone to the capture zone. The devices of this invention also include multilane flow paths and multiple capture zones to quantitate analyte.

21 Claims, 4 Drawing Sheets

U.S. PATENT DOCUMENTS

| | | |
|---|---|---|
| 4,806,311 A | 2/1989 | Greenquist |
| 4,861,711 A | 8/1989 | Friesen et al. |
| 4,883,688 A | 11/1989 | Houts et al. |
| 4,943,522 A | 7/1990 | Eisinger |
| 4,959,307 A | 9/1990 | Olson |
| 5,200,317 A | 4/1993 | Georgevich |
| 5,217,905 A | 6/1993 | Marchand et al. |
| 5,229,073 A * | 7/1993 | Luo et al. ............... 422/56 |
| 5,252,496 A * | 10/1993 | Kang et al. ............ 436/529 |
| 5,310,650 A | 5/1994 | McMahon et al. |
| 5,384,264 A | 1/1995 | Chen |
| 5,500,350 A | 3/1996 | Baker |
| 5,521,102 A | 5/1996 | Boehringer |
| 5,559,041 A | 9/1996 | Kang |
| 5,602,040 A | 2/1997 | May |

FOREIGN PATENT DOCUMENTS

| | | |
|---|---|---|
| WO | WO8808534 A1 * | 11/1988 |
| WO | WO-94/28415 | 5/1994 |

OTHER PUBLICATIONS

Brown et al., "Natural family planning," American Journal of Obstetrics and Gynecology Oct. 1997, Part 2.

International Search Report for PCT/US98/04441, mailed on Jul. 20, 1998, 2 pages.

Lou et al., Clin. Chem. (1993) 39:619-624.

Muggio et al., "Enzyme-Immunoassay," CRC Press, 1987, pp. 61, 184, 185.

* cited by examiner

VARIANT

QUANTITATIVE LATERAL FLOW ASSAYS AND DEVICES

This is a continuation application of U.S. Ser. No. 08/812,616, filed Mar. 6, 1997, issued as U.S. Pat. No. 6,924,153 on Aug. 2, 2005, which is hereby incorporated by reference in its entirety.

BACKGROUND OF THE INVENTION

1. Field of the Invention

This invention relates to the field of solid phase binding assays using ligands and their specific binding receptors. In particular, it relates to the use of such assays to detect in a quantitative or semi-quantitative manner the amount of an analyte in a sample suspected of containing the analyte.

The ability to employ naturally occurring receptors or antibodies directed against specific compounds in assaying for the presence of a compound of interest has created a burgeoning immunoassay business. In these assays, a homologous pair of specific binding pair members ("sbp members"), usually an immunological pair, comprising a ligand and a receptor (antiligand) is involved, wherein one of the sbp members is labelled with a label which provides a detectable signal. The immunoassay methodology results in a distribution of the signal label between signal label bound in a complex of the sbp members and unbound signal label. The differentiation between bound and unbound signal label can be a result of physical separation of bound from unbound signal label or modulation of the detectable signal between bound and unbound signal label.

For the most part, immunoassays that have been directed towards quantitative determinations have required complex instrumentation, relatively sophisticated equipment, careful experimental technique and skilled operators, such as is found in clinical laboratories. Therefore, quantitative and semi-quantitative immunoassays have found less extensive application in settings such as the home, a medical practitioner's office, a health care maintenance organization setting or a primary care setting in a hospital where complex instrumentation is unavailable and testing is typically done by untrained personnel. Even in a clinical laboratory, simple and rapid tests for screening diagnostic, monitoring or prognosis for outcome purposes done by inexperienced personnel could provide substantial economies in terms of timeliness of results and labor costs.

In developing an immunoassay, there are many considerations. One consideration is to provide substantial differentiation between the observed signal resulting from signal label when bound as compared to unbound. Another consideration is to minimize interference from endogenous materials in the sample suspected of containing the compound of interest. A further consideration is the ease with which the observed signal can be detected and serve to differentiate between concentrations in the concentration range of interest. Other factors include the ease of preparation of reagents, the precision with which the samples and reagents must be prepared and measured, the storage stability of the reagents, the number of steps required in the protocol, and the proficiency with which each of the steps must be performed. Therefore, in developing a quantitative assay that can be used by untrained personnel, such as assays to be performed in the home, medical offices and the like, the observed result should be minimally affected by variations in the manner in which the protocol is carried out and the techniques for performing the various steps should be simple. Preferably, one-step protocols should be employed.

Recently, a variety of solid phase binding assays which do not require complex instrumentation have been described for detection of analyte in a sample suspected of containing the analyte. However, such assays typically provide qualitative results. Frequently, such solid phase assays also employ a multiplicity of steps, such as wash steps, to separate unbound label from bound label. Therefore, it would be desirable to provide simple, one-step solid phase non-instrumented methods and devices for quantitating an analyte in a sample suspected of containing the analyte. This invention fulfills that and other needs.

2. Summary of Related Art

A Noninstrumented Quantitative Test System and Its Application for Determining Cholesterol Concentration in Whole Blood; M. P. Allen et al.; *Clinical Chemistry*, Vol 36 No. 9: 1591–1597 (1990); discloses a noninstrumental solid phase method of quantitating cholesterol using enzymatic conversion of immobilized substrate.

One-Step Competitive Immunochromatographic Assay for Semiquantitative Determination of Lipoprotein(a) in Plasma; S. C. Lou et al.; *Clinical Chemistry*, Vol. 36 No. 4: 619–624 (1993); discloses semiquantitative measurement of lipoproteins using a solid phase assay with multiple capture bars.

Immunochemical semi-quantitative Assay Method—and appts.; Patent No. WO 94/28415A to H. Manita; discloses a semiquantitative chromatographic immunochemical assay method which consists of passing the sample for assay through a predetermined amount of an immobilized antibody (IAb) which recognizes the substance to be assayed, then allowing the excess to pass to a label (such as a color indicator) which indicates its presence.

Concentrating Immunochemical Test Strip; European Patent No. EP 0 191 640 A2 to D. Calderhead et al. (1986); discloses solid phase methods and devices for detecting analytes involving contacting a test strip containing a first sbp member with a test solution comprising the analyte and a second sbp member complementary to the analyte. The first sbp member is capable of binding the second sbp member.

U.S. Pat. No. 4,861,711; H. Friesen et al. (1989); discloses a solid-phase diagnostic device for the determination of biological substances.

U.S. Pat. No. 4,740,468; L. Weng et al. (1988); discloses a solid phase specific binding method and device for detecting an analyte.

U.S. Pat. No. 4,806,311; A. Greenquist (1989); discloses a multi-zone test device for analyte determination using a labelled reagent and immobilized reagent which are specific binding partners whose binding to each other depends on the amount of analyte present and a detection zone with an immobilized binding substance for the labelled reagent.

U.S. Pat. No. 4,168,146; A. Grubb et al. (1979); discloses a solid phase method and strip with bound antibodies.

U.S. Pat. No. 4,959,307; J. Olson (1990); discloses a solid phase method and device for detecting an analyte involving contacting a test solution containing sample, antibody to the analyte and a labelled analyte with a test strip containing an immobilized first receptor that binds to the labelled analyte and an immobilized second receptor that binds to the antibody.

U.S. Pat. No. 4,435,504; R. Zuk (1984); discloses a chromatographic immunoassay employing a sbp member and a label conjugate.

U.S. Pat. No. 4,883,688; T. Houts et al. (1989) discloses an immunochromatographic device which quantitates analyte as a function of the distance migrated by a sbp member along the device.

SUMMARY OF THE INVENTION

The present invention generally provides methods devices and kits for visually quantifying the amount on an analyte in a sample. For example, in one aspect, the present invention provides a method of determining an amount of an analyte in a sample, wherein the analyte is a member of a specific binding pair (sbp member). The method comprises providing a lateral flow matrix which defines a flow path and which comprises in series, a sample receiving zone, a labeling zone, and one or more serially oriented capture zones. The labeling zone comprises a diffusively bound labeled first sbp member that is complementary to or analogous to the analyte. Each of the one or more capture zones comprises at least a second sbp member immobilized in the capture zone, the second sbp member being complementary to the analyte. The sample is contacted with the sample receiving zone, whereby the sample flows along the flow path. Quantitation is carried out by observing the pattern of label that accumulates at the one or more capture zones and correlating that pattern to the amount of analyte in the sample.

In a related aspect, the methods of the invention are as described above, except that the labeling zone comprises a diffusively bound labeled first sbp member that is complementary to the analyte, and each of the one or more capture zones comprises at least a second sbp member immobilized in the capture zone, the second sbp member being analogous to the analyte. Quantitation is then carried out as above.

In another alternate aspect, the methods of the invention provide a lateral flow matrix which defines a flow path and which comprises in series, a sample receiving zone, a labeling zone, a barrier zone and one or more serially oriented capture zones. In this aspect, the labeling zone comprises a diffusively bound labeled first sbp member that is complementary to the analyte, the barrier zone comprises a second sbp member analogous to the analyte immobilized in the barrier zone, and each of the one or more capture zones comprises at least a third sbp member immobilized in the one or more capture zones, the third sbp member being capable of binding the first sbp member.

In yet another aspect, the labeling zone comprises a diffusively bound labeled first specific binding pair member that is analogous to the analyte, the barrier zone comprises a second specific binding pair member that is complementary to the analyte, and each of the one or more capture zones comprises at least a third specific binding pair member immobilized in the one or more capture zones, the third specific binding pair member being complementary to the analyte.

The methods of the invention also provide lateral flow matrices which define a flow path and which comprise in series, a sample receiving zone, a labeling zone and at least first and second serially oriented capture zones. In this aspect, the labeling zone comprises a diffusively bound labeled first sbp member that is complementary to the analyte whereby the first spb member and the analyte form an analyte-first spb member complex. The first capture zone comprises a second sbp member immobilized therein which is capable of binding the analyte-first sbp member complex with a first affinity, and the second capture zone comprises a third sbp member that is capable of binding the analyte-first spb member complex with a second affinity. In this aspect, the second affinity is typically different from the first affinity.

In addition to providing the methods described above, the present invention also provides devices for practicing these methods, i.e., for use in visually quantifying an amount of an analyte in a sample, and kits incorporating these devices.

DESCRIPTION OF THE PREFERRED EMBODIMENT

Figure 1:
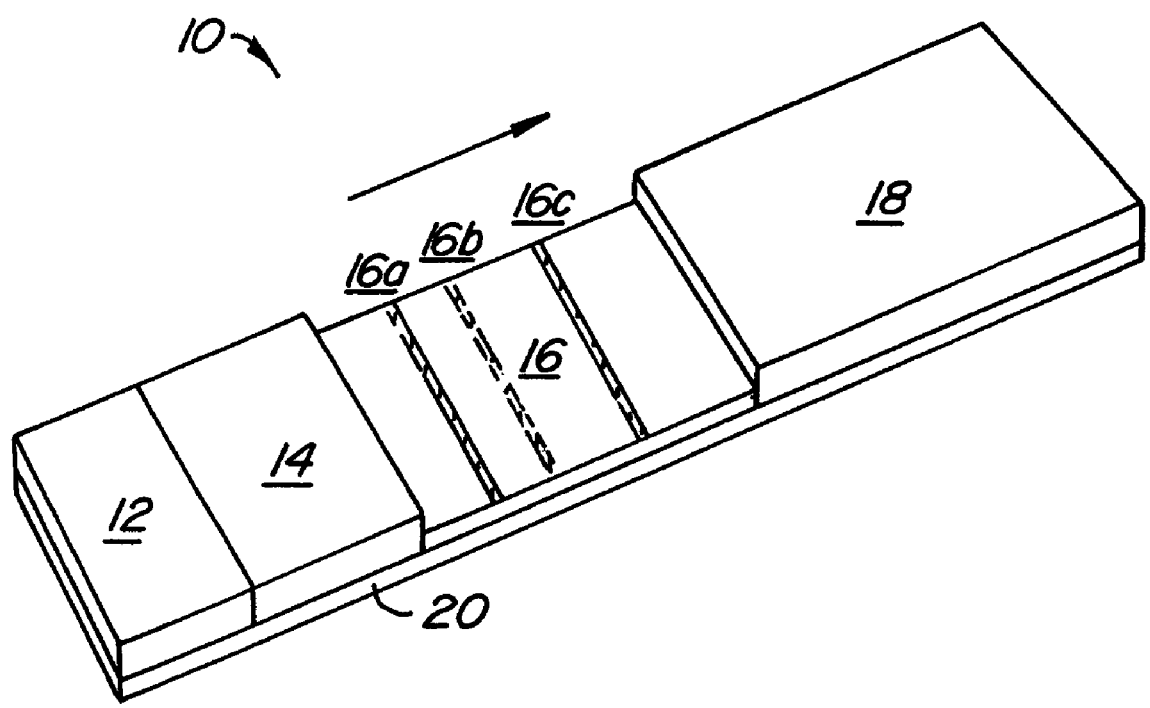
FIG. 1 shows a single lane lateral flow assay device for visually quantitating analytes in accordance with the principles of this invention with a sample receiving pad 12, a labelling zone 14, a capture zone 16 with capture lines 16a, 16b and 16c and an absorbent zone 18.

This invention relates to solid phase specific binding pair lateral flow assays for the visual quantitative and semiquantitative determination of high and low molecular weight analytes in samples suspected of containing such analytes.

In describing the various aspects of the present invention, a number of terms will be generally defined as follows:

"Sample suspected of containing an analyte" shall mean any sample that is reasonably suspected of containing an analyte which can be analyzed by the method of the present invention. Such samples can include human, animal or man-made samples. The sample can be prepared in any convenient medium which does not interfere with the assay. Typically, the sample is an aqueous solution or biological fluid as described in more detail below.

The fluid sample may be a biological fluid such as, but not limited to, whole blood, serum, plasma, nasal secretions, sputum, urine, sweat, saliva, transdermal exudates, pharyngeal exudates, bronchoalveolar lavage, tracheal aspirations, cerebrospinal fluid, vaginal or urethral secretions, or the like. Herein, fluid homogenates of cellular tissues such as, for example, hair, skin and nail scrapings, meat extracts and skins of fruits and nuts are also considered biological fluids. Fluid samples also include nonbiological fluids such as, for example, soil extracts and water supplies. Multiple different analytes may be detected from a single fluid sample.

"Specific binding pair member" shall mean a molecule (sbp member) which is one of two different molecules, having an area on the surface or in a cavity which specifically binds to and is thereby defined as being complementary with a particular spatial and polar organization of the other molecule. The two molecules are related in the sense that their binding to each other is such that they are capable of distinguishing their binding partner from other assay constituents having similar characteristics. The members of the specific binding pair are referred to as ligand and receptor (antiligand), sbp member and sbp partner, and the like. A molecule may also be a sbp member for an aggregation of molecules; for example an antibody raised against an immune complex of a second antibody and its corresponding antigen may be considered to be an sbp member for the immune complex. Complementary sbp members bind to each other, as for example, a ligand and its complementary receptor, such as biotin and avidin/streptavidin, antigen and antibody against that antigen. Sbp members will usually be members of an immunological binding pair such as an antigen-antibody, although other specific binding pairs, such as biotin-avidin, hormones-hormone receptors, nucleic acid duplexes, IgG-protein A, and the like are specific binding pairs which are not immunological binding pairs. An sbp member is analogous to another sbp member if they are both capable of binding to another identical complementary sbp member. Such an sbp member may, for example, be either a ligand or a receptor that has been modified by the replacement of at least one hydrogen atom by a group to provide, for example, a labelled ligand or labelled receptor. The sbp members can be analogous to or complementary to the analyte or to an sbp member that is complementary to the analyte. Different combinations of sbp members maybe used in the same assay or test device.

The present assays can be used for the quantitation and semiquantitation of any analyte for which a specific binding partner exists. Analytes may be polyvalent or monovalent. Polyvalent analytes include polypeptides and proteins, polysaccharides, nucleic acids, antibodies, microorganisms, bacteria, viruses and combinations thereof. Monovalent analytes include drugs, haptens, pesticides, pollutants, steroids, vitamins and the like. Descriptions and listings of representative analytes are found in U.S. Pat. Nos. 4,299,916, 4,275,149, 4,806,311, all incorporated by reference.

The term "analyte analog" or "ligand analog" refers to a modified analyte or analyte surrogate or modified ligand or ligand surrogate that can compete with the analyte for binding to an sbp member complementary to the analyte or ligand, such as an antibody against the analyte. The modification typically provides a means for attaching the analyte or ligand to another molecule, such as, for example, a label, or surface. The term "analyte surrogate" or ligand surrogate" refers to a compound that can specifically bind to a receptor complementary to the analyte or ligand. Thus, the analyte surrogate or ligand surrogate binds to the receptor in a manner similar to the analyte or ligand. The surrogate could be, for example, an antibody directed against the idiotype of an antibody to the analyte or ligand. Combinations of ligand analogs may be used.

The term "ligand" as used herein, means any compound for which a receptor naturally exists or can be prepared.

"Antigen" shall mean any compound capable of binding to an antibody, or against which antibodies can be raised.

"Receptor" shall mean any compound or composition capable of recognizing a particular spatial or polar orientation of a molecule, e.g., epitopic or determinant site. Illustrative receptors include: antibodies, enzymes, thyroxine binding globulin, intrinsic factor, lectins, nucleic acids, protein A, complement, complement C1q, and the like. Receptors are also referred to as antiligands.

"Antibody" shall mean an immunoglobulin having an area on its surface or in a cavity that specifically binds to and is thereby defined as complementary with a particular spatial and polar organization of another molecule. The antibody can be polyclonal or monoclonal. Antibodies may include a complete immunoglobulin or fragments thereof, which immunoglobulins include the various classes and isotypes, such as IgA (IgA1 and IgA2), IgD, IgE, IgM, and IgG (IgG1, IgG2, IgG3, and IgG4) etc. Fragments thereof may include Fab, Fv and F(ab')$_2$, Fab', and the like. Antibodies may also include chimeric antibodies made by recombinant methods.

The terms "impregnated" or "diffusively bound" or "freely suspendible" are meant to refer to a state of permeation or reversible surface adherence. Substances which are impregnated or diffusively bound are not immobilized within or upon the support matrix, but are capable of being mixed or suspended in fluids placed on the support matrix.

"Ancillary materials" shall mean any materials that may be employed in an assay in accordance with the present invention. For example, buffers will normally be present in the labelling means, the neutralization means, as well as stabilizers for the assay medium and assay components. Frequently, in addition to these additives, additional proteins, such as albumins, or surfactants, non-ionic or ionic, binding enhancers, e.g. polyalkylene glycols, or the like, may be present, including free antibodies, analyte analogs, or other unrelated ligands, for the purpose of removing or adding materials or to modify the amount, postition, partitioning, or appearance of the analyte or other compounds used in the invention.

Generally, the devices and methods of the present invention of the present invention employ lateral flow assay techniques and matrices capable of bibulous and/or non-bibulous lateral flow as generally described in U.S. Pat. Nos. 5,424,193, 4,943,522; 4,861,711; 4,857,453; 4,855,240; 4,775,636; 4,703,017; 4,361,537; 4,235,601; 4,168,146; 4,094,647; co-pending application U.S. Ser. No. 07/639,967, European Patent Application Nos. 451,800; 158,746; 276, 152; 306,772 and British Patent Application No. 2,204,398; each of which is incorporated herein by reference.

It is a general object of the present invention to provide methods, devices, systems and kits which can be used to visually quantify or semi-quantify an amount of an analyte of interest in a particular sample. Although these systems are generally described in terms of visual quantification, it will be readily appreciated that other detection systems, optical or otherwise, may be used in such quantitation.

The present invention can be practiced in a variety of assay formats including sandwich and competitive modes. In one aspect of a competitive format, a labelled analyte analog and an analyte will compete for binding to a limited amount of binding sites on a complementary specific binding pair member. As explained in more detail below, the complementary sbp member is immobilized on a solid phase in a manner which allows for the direct quantitative or semi-quantitative read out of the amount of analyte present in the sample. In a sandwich assay, the sample suspected of containing the analyte is contacted with a complementary first sbp member to form a complex between the analyte and the first sbp member. Generally, the first sbp member is labelled. This complex is then contacted by a second sbp member, which is generally complementary to the analyte, bound to a solid support, which effects separation of the bound first sbp member from the unbound first sbp member.

In the immunometric mode, a labelled antibody to the analyte is used as the first sbp member and analyte or analyte analog is immobilized on the solid phase to capture unbound labelled antibody. This effects separation of bound labelled antibody from unbound labelled antibody. Analyte concentration may be directly determined by detection of the amount of labelled antibody captured by the immobilized analyte. Optionally, a third sbp member which binds to the complex between analyte and labelled antibody may also be immobilized on the solid phase. As described in more detail below, detection of the amount of complex bound to the third sbp member provides an alternative method of quantitating analyte present in the sample. Similarly, combinations of third sbp members or ligands, antiligands, antiglobulins or ligand analogs maybe used to facilitate, define and/or control analyte separation directly or indirectly for quantitation by providing the means of controlling the efficiency of separation. In order to more fully describe and explain the assay formats capable of being employed in the invention, a variety of specific embodiments will now be described in more detail.

Sandwich Assay Format

One aspect of the invention employs a sandwich assay format. The sample is mixed with a labelled first specific binding pair member for the analyte and allowed to traverse a lateral flow matrix, past a series of spatially separated capture zones located on the matrix. The sample may be mixed with the labelled first sbp member prior to addition of the sample to the matrix. Alternatively, the labelled first sbp member may be diffusively bound on the matrix on a labelling zone at a point upstream of the series of capture zones. Sometimes, the sample is added directly to the labelling zone. Preferably, the sample is added to a sample receiving zone on the matrix at a point upstream of the labelling zone and allowed to flow through the labelling zone. The labelled first sbp member located within the labelling zone is capable of being freely suspendible in the sample. Therefore, if analyte is present in the sample, the labelled first sbp member will bind to the analyte and the resulting analyte-labelled first sbp member complex will be transported to and through the capture zones. The extent of complex formation between the analyte and the labeled sbp member is directly proportional to the amount of analyte present in the sample. A second sbp member capable of binding to the analyte-first sbp member complex is immobilized on each of the capture zones. This second sbp member is not capable of binding the labelled sbp member unless the labelled sbp member is bound to the analyte. Thus, the amount of labelled sbp member that accumulates on the capture zones is directly proportional to the amount of analyte present in the sample.

The analyte-labelled first sbp member complex flows sequentially through the series of capture zones and becomes bound to the capture zones. The first capture zone binds to and depletes some of the complex in the sample. Therefore, the concentration of complex which reaches the second capture zone is lower, having been depleted by the quantity of the complex which bound to the first capture zone, and the rate of binding of complex to the second capture zone is lower than the rate of binding of complex to the first capture zone. As such, for a given amount of analyte in the sample, detectable signal takes longer to appear on the second capture zone relative to the first capture zone.

Similarly, the concentration of complex reaching the third capture zone is also depleted relative to the concentration that reached the second capture zone and signal will take even longer to appear. In this fashion, it is apparent that for a given concentration of analyte in the sample, a downstream capture zone will take longer to produce a detectable signal compared to a capture zone that is upstream from it. Similarly, as the concentration of analyte in the sample increases and the amount of analyte-labelled first sbp member complex reaching the capture zones increases, detectable signal will appear earlier at a particular capture zone. Therefore, if the matrix is inspected at a predetermined time after sample addition, different analyte concentrations will produce a different pattern of signal on the series of capture zones. For example, a low concentration of analyte may only produce signal on the two most upstream capture zones, a higher analyte concentration may produce signal on the three most upstream capture zones, an even higher analyte concentration will produce signal on the four most upstream capture zones, and so on. Therefore, the number of lines with detectable signal is proportional to the amount of analyte present in the sample. The pattern of lines observed constitutes the composite signal that is correlated to the analyte concentration. Uniform color development on each line may be obtained by modifying the concentration or binding affinity of the sbp member binding reagent on each capture zone. As shown in the Examples, one may also inspect the strip at different time points and correlate the number of lines at which color is produced at different times with the amount of analyte present in the sample. The pattern of lines which produce signal can be correlated with the analyte concentration with the aid of a chart or other tabulation which allows the user to visually determine the analyte concentration by comparison to the chart; for example signal on the two most upstream lines indicates a certain analyte concentration, whereas signal on the three most upstream lines indicates another higher analyte concentration etc. Such charts or tables can be used with all embodiments of this invention described herein which correlate the number or pattern of lines showing signal with analyte concentration.

Adjustment of the concentrations of the labelled sbp member and the immobilized second sbp member allows one to control the quantity and rate at which color is produced at the capture zones for a given analyte concentration and thus to quantitate analyte within specific ranges. Typically, the amount of labelled specific binding pair member used is sufficient to bind all of the analyte that is expected to be present. For example, IgE is typically measured at 20–100 IU/ml urine; hCG at 10–200 mIU/ml urine and PDG at 1–20 µg/ml urine. The concentration, affinity and combination of binding reagents may be experimentally determined to facilitate separation. Increasing the amount of second specific binding pair member immobilized in the capture zone will increase the efficiency of capture and produce signal more rapidly. The amount of second sbp member on the capture zone(s) can be adjusted to allow for discrimination between various ranges of analyte concentration. It is also possible to increase the discrimination between different analyte concentrations and provide sharper "cut offs" between those concentrations by immobilizing second sbp members of increasing affinity for the analyte on the capture zones as one proceeds in downstream sequence. One can also provide intermediate capture zones masked off from visual observation facilitating the efficiency of separation and color development.

Alternatively, combinations of reagents may be immobilized on the capture zone(s). For example, the first capture line may employ an antiglobulin and the second capture line may employ avidin both as a means to differentially capture labelled biotinylated globulins specific to an analyte and their complexes with analyte. Similar considerations apply to other assay formats and devices disclosed herein which rely on capturing a labelled sbp member or complex thereof by one or more multiple capture zones arranged in downstream sequence.

In this format, the analyte is generally a polyvalent analyte, such as protein or hormone, with multiple binding sites for the sbp members, wherein binding of the first sbp member does not interfere with the binding of the second sbp member. For example, when the analyte is IgE, the first sbp member may be an antibody against one epitope of the IgE and the second sbp member may be an antibody against a different epitope. Alternatively, the second sbp member may be an antibody specifically against the complex formed between IgE and the first sbp member.

This invention also provides a device for quantitating analyte concentrations as shown in FIG. 1. With reference to FIG. 1, the devices comprise a matrix capable of lateral non-bibulous flow comprising a sample receiving zone 12, an labelling zone 14, a capture zone 16 and optionally an absorbent pad 18 in fluid contact and arranged in downstream sequence as shown. The labelling zone has diffusively bound therein a labelling reagent, which in the case of the sandwich assay described above is an sbp member complementary to the analyte. Analyte in the sample flows to the labelling zone 14, binds to the labelled complementary sbp member therein and flows to the capture zone 16. The capture zone has immobilized therein a second sbp member complementary to the analyte as described above. The capture zone will comprise a series of spatially separated capture lines 16a, 16b, 16c and so on each of which has the second sbp member immobilized therein. The density of the second sbp member on the capture zones can vary or different second sbp members of increasing affinity for the analyte can be present in the sequence 16a<16b<16c and so on. Combinations of different ligand anti-ligand pairs may be used, such as second sbp members (e.g., antibodies) recognizing different epitopes of the analyte, the binding constants for which are varied. In this arrangement, there is no second sbp member immobilized on the segments of the matrix between the capture lines. The second sbp member binds the analyte-labelled first sbp member complex thus producing a visually detectable signal. As described earlier, when multiple capture lines are used as the detection zone, the pattern on lines on which signal is detected may be used to visually quantitate the analyte concentration, e.g., by comparing the pattern to a calibrated chart.

Competitive Formats

Another aspect of the invention employs a competitive format. The sample is mixed with a labelled analyte analog capable of binding to a first specific binding pair member complementary to the analyte and allowed to traverse a bibulous or non-bibulous matrix capable of lateral flow (also termed "a lateral flow matrix"), past a series of spatially separated capture zones located on the matrix. The sample flows sequentially past the series of capture zones. The sample may be mixed with the labelled analyte analog prior to addition of the mixture to the matrix. Alternatively, the labelled analyte analog may be diffusively bound to the matrix on a labelling zone at a point upstream of the series of capture zones. Sometimes, the sample is added directly to the labelling zone. Preferably, the sample is added to a sample receiving zone on the matrix at a point upstream of the labelling zone and allowed to flow through the labelling zone. The labelled analyte analog located on the labelling zone is capable of being freely suspendible in the sample.

A first specific binding pair member complementary to the analyte is immobilized on the capture zones. Sample and labelled analyte analog flow to and through the capture zones and compete for binding to the immobilized first sbp member. The rate of capture of labelled analyte analog by the capture zones is inversely proportional to the analyte concentration. At high analyte concentrations, the upstream capture zones are preferentially bound by analyte and detectable signal appears later on these capture zones. Labelled analyte analog competes effectively for binding at the downstream capture zones only after analyte has been depleted by binding at the upstream capture zones. This can be used to control the timing and rate of bound/free separation. Viewed alternatively, high analyte concentrations result in visually detectable signal appearing at the downstream capture zones as well as the upstream capture zones. Whereas at low analyte concentrations, labelled analyte analog is able to compete more effectively for binding to the upstream capture zones and is captured at those capture zones. As a result, at low analyte concentrations, the labelled analyte analog either does not produce visually detectable signal at, or takes longer to produce visually detectable signal at the more downstream capture zones. As explained above, the number of capture zones showing detectable signal provides a visual direct readout of the analyte concentration. Higher analyte concentrations lead to detectable signal appearing at more capture zones. Concentrations of the labelled analyte analog and the amount of immobilized sbp member as well as the number and type of capture zones can be adjusted by one of skill on the art to allow for quantitation of analyte in the desired range.

In another embodiment, the sbp member is immobilized uniformly on a single capture zone on the matrix instead of being located on a series of spatially separated zones. Analyte competes with labelled analyte analog for binding to the immobilized sbp member. In this embodiment, the distance traversed by the labelled analyte analog prior to capture is directly proportional to the analyte concentration. The binding constants of the analyte and the labelled analyte analog to the sbp member and the gradient of the capture reagent provides for differential separation under non-chromatographic conditions. The signal detected from the labelled analyte analog serves as a "footprint" on the matrix of the distance traversed by the labelled analyte analog and this distance can be read off directly. Therefore, the analyte concentration is directly measurable by comparing the distance travelled by the labelled analyte analog to a suitable calibration curve obtained by using known quantities of analyte.

Another aspect of a competitive assay format employs an immobilized sbp member on an intermediate "barrier" zone located on the matrix downstream of the labelling zone and upstream of a detection zone. The barrier zone, whether a labelled analyte analog, or a labelled sbp member complementary to the analyte, serves as a means of preventing a labelled species from migrating further along the matrix unless the analyte concentration exceeds a certain threshold level.

In one aspect of this embodiment, labelled analyte analog, such as a labelled antigen, is provided, for example, by binding it to dyed latex beads either directly or through a carrier protein. Alternatively, the target specific labelling complex disclosed in PCT publication WO 94/01775 can be used. The target specific antigen complex is preferably used when the analyte is an antibody. The labelled antigen may be deposited onto the matrix in a labelling zone downstream of the sample receiving zone and upstream of the detection zone or premixed with the sample. A barrier zone comprising an sbp member complementary to the analyte, such as an antibody, is deposited onto the matrix downstream of the labelling zone. The third zone, the detection zone, which is downstream of the barrier zone, comprises a binding substance for the labelled antigen. Sample mixes with labelled antigen and passes first through the barrier zone. When no antigen is present in the sample, all the labelled antigen will bind to the barrier zone. The amount of antibody on the barrier zone must be sufficient to bind all the labelled antigen when antigen is not present in the sample. Usually, this zone will be masked off from view and will not be visible in the test device. If antigen is present in the sample, labelled antigen competes with sample antigen for the antibody immobilized in the barrier zone. If the sample contains antigen above a threshold level, the barrier zone antibody is unable to capture all of the labelled antigen. This level is controlled by the relative ratios of antigen and labelled antigen as well as the concentration and affinity of the barrier zone antibody. For a given level of labelled antigen, as barrier zone antibody density increases higher levels of sample antigen will be required for the barrier zone threshold level to be exceeded. The density, concentration, amount and/or affinity of barrier zone reagent (antibody in this example) is adjusted such that 100% bound/free separation is effected at antigen concentrations below the desired threshold level. These parameters can be varied by one of skill in the art to quantitate sample analyte in the desired range.

Thus, when the breakthrough threshold analyte concentration is exceeded, some of the labelled antigen evades capture at the barrier zone antibody and flows through to the detection zone. The detection zone contains a binding substance for the labelled species (in this case, labelled antigen) that evades capture at the barrier zone when the threshold analyte concentration is exceeded. This binding substance can be a specific binding pair member for the antigen, the label or the carrier protein linking the antigen to the latex bead, or a receptor for a ligand on the labelled antigen. Frequently this sbp member is an antibody. If there is a sufficient amount of free antigen in the sample, then the detection zone will be visible indicating a positive test result. The amount of the antibody deposited on the detection zone can be adjusted in such a way that labelled antigen which does not bind to the barrier zone is in excess at the detection zone. Then, if multiple detection zones (second, third, fourth and so on) are present in downstream sequence, labelled antigen will migrate to the successive detection zones depending on the amount of labelled antigen present thus allowing a semi-quantitative assay with multiple lines. As described earlier, the visual detection zones can have antibodies of increasing affinity arranged in downstream sequence to provide for good discrimination between analyte concentrations. Alternatively, the detection zones can have in downstream sequence combinations of reagents, e.g., antibodies to different epitopes, followed by streptavidin, a capture zone of higher binding affinity or enhanced binding affinity, to efficiently remove finite quantities of labelled antigen even though labelled antigen concentration diminishes as the sample flows downstream.

Immunometric Formats

Other embodiments of the present invention employ a format of the immunometric type. In these embodiments, analyte in the sample is first allowed to bind to labelled sbp member complementary to the analyte to form an analyte-labelled sbp member complex. The amount of unbound labelled sbp member remaining is inversely proportional to the amount of analyte in the sample. The labelled sbp member may be premixed with the sample or it may be diffusively bound to the matrix in the labelling zone upstream of the capture zone and downstream of the sample receiving zone. The analyte-labelled sbp member complex is then allowed to flow through a capture zone which comprises an immobilized analyte analog which is capable of binding to the unbound labelled sbp member. Generally, the immobilized analyte analog is not able to bind to the labelled sbp member bound to the analyte, thereby effecting a separation between bound and unbound label.

In one aspect of this embodiment, the immobilized analyte analog is located on a series of spatially separated capture zones arranged in downstream sequence and the test solution comprising the sample and labelled sbp member flows sequentially through the series of capture zones. As analyte concentration increases, color appears on a greater number of capture zones. Immobilized analyte analog competes with the analyte for binding to free labelled sbp member. Free labelled sbp member, if present, is bound at the more upstream capture zones. As analyte concentration increases, more labelled sbp member reaches the downstream capture zones in the form of analyte-labelled sbp member complex. As a result, greater amounts of labelled sbp member reach the downstream capture zones. Without being bound by any one particular theory, it is believed that as the complex flows downstream analyte dissociates from the labelled sbp member complex and is bound at the capture zone. Immobilized analyte analog on the downstream capture zones is thus able to compete for binding to the labelled sbp member. Since different antibodies typically have different on/off rates, quantitation is antibody dependent and one uses an antibody with the correct off rate for the analyte in the concentration range being quantitated. Off rates are determined empirically and the correct antibody selected experimentally for each case. Increasing analyte concentration thereby correlates with the appearance of detectable signal on an increasing number of downstream capture zones. As described earlier, and shown in more detail in the Examples, the number of capture zones on which signal can be detected due to capture of the labelled sbp member can be correlated with varying ranges of analyte in the sample by varying the number of capture zones, and the concentrations of labelled sbp member and immobilized analyte analog by protocols known to those skilled in the art.

In another embodiment of this type of assay, an analyte analog is immobilized on a intermediate zone (hereinafter the "barrier zone") downstream of the sample receiving zone and labelling zone and upstream of a detection zone. Analyte analog on the barrier zone is able to bind free labelled sbp member. Generally, there is sufficient analyte analog on the barrier zone to bind all the labelled sbp member in the absence of analyte. Bound labelled sbp member flows through the barrier zone in the form of an analyte-labelled sbp member complex which is unable to bind to the immobilized analyte analog. The detection zone contains an immobilized sbp member that is capable of binding the analyte-labelled sbp member complex. The concentration of sbp member on the labelled sbp member can be controlled to effect 100% bound/free separation on the barrier zone thus providing a sharp cut off at the analyte threshold level. The immobilized sbp member on the detection zone may be a specific binding substance for the label, an antibody against an exposed epitope of the analyte in the analyte-labelled sbp member complex, an antibody against a carrier protein that links the label to the sbp member, an antibody against the species of the labelled sbp member (when the labelled sbp member is a labelled antibody), a receptor for a ligand on the labelled sbp member, and the like. Higher analyte concentrations lead to higher concentrations of analyte-labelled sbp member complex and thus more detectable signal at the detection zone(s). The amount of signal is directly proportional to the sample analyte concentration. Either the intensity of signal at the detection zone, the time at which a detectable signal appears on the detection zone or the number of detection zones can be used to visually quantitate the analyte concentration in the sample by comparison to a calibration curve obtained by using known amounts of analyte.

In this format, the analyte may be either a polyvalent analyte such as a protein or a hormone, or a monovalent analyte such as a small drug, steroid or hormone. For example, when the analyte is HCG, the labelled sbp member can be latex-labelled mouse (IgG) anti-HCG, the barrier zone can contain immobilized HCG and the detection zone will contain immobilized goat anti-mouse IgG (Fc). The goat anti-mouse IgG will be able to capture the HCG-mouse (IgG) anti-HCG immune complex. Using an anti-mouse IgG directed against the Fc portion of the mouse antibody increases the efficiency of capture because there is less likelihood of interference to binding from the HCG already bound to the mouse IgG at its antigen binding region. As shown in the Examples, a similar scheme can be employed for quantitating a small molecule, as is shown for progesterone. In this case, a progesterone-BSA conjugate is immobilized on the barrier zone and goat anti-mouse IgG (Fc) on the detection zone. As with the previous embodiments, one skilled in the art will be able to readily quantitate analyte in a desired range by varying the concentrations of labelled sbp member and immobilized analyte analog. An advantage of this approach is that one can use just one sbp member for either high or low molecular weight analytes providing improved specificity and simpler reagent development.

Figure 4:
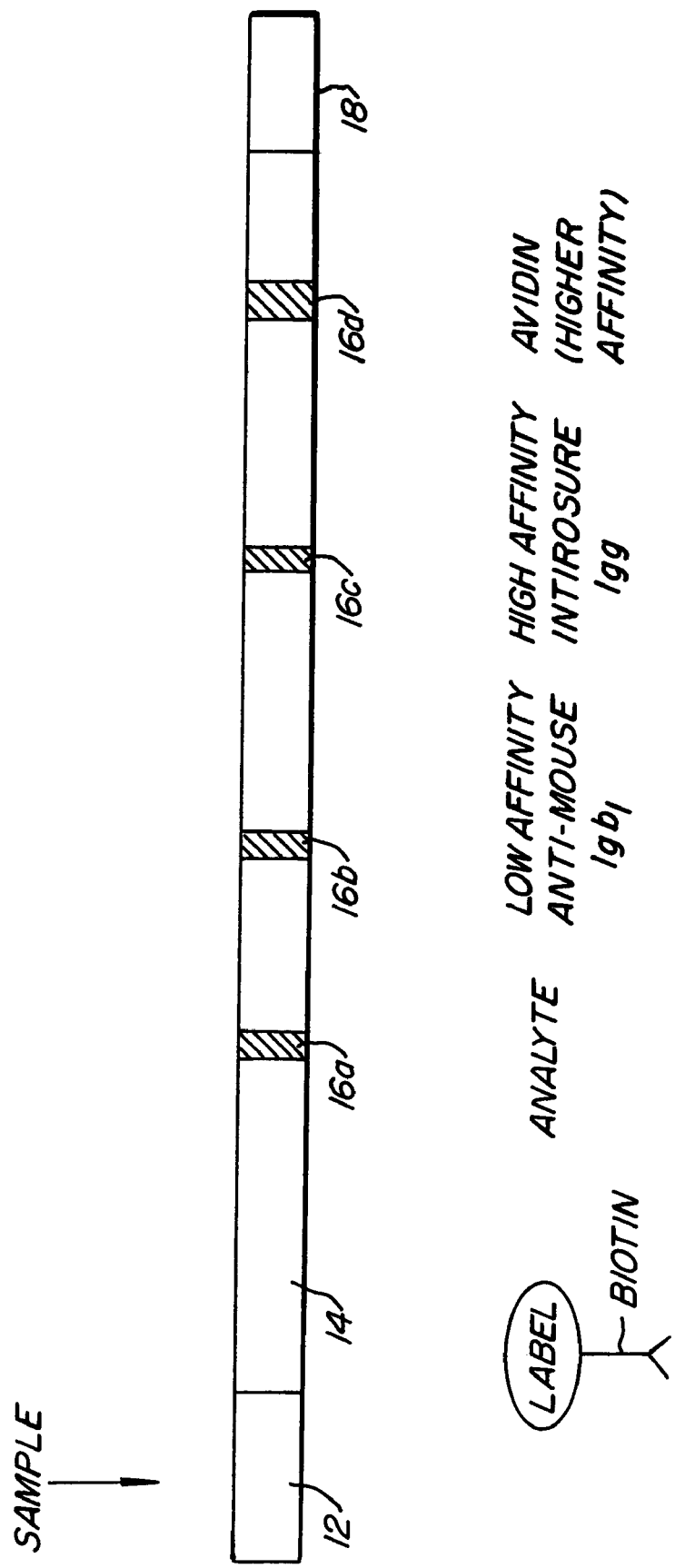
FIG. 4 shows an example of a flow path with detection zones having capture reagents of increasing affinity arranged in downstream sequence. The flow path has a sample receiving zone 12, a labelling zone 14 having a labelled biotinylated anti-analyte mouse IgG antibody, a barrier zone 16a having immobilized analyte or analyte analogue and detection zones 16b1, 16b2 and 16b3. 16b1 has monoclonal anti-mouse IgG of low affinity; 16b2 has polyclonal anti-mouse IgG of high affinity; and 16b3 has streptavidin of very high affinity.

Optionally, the detection zone may be a series of spatially separated zones arranged in downstream sequence as described earlier. Again, as described earlier, the rate at which signal appears on the downstream zones and the number of such zones on which signal is detected after a predetermined time can be correlated with the amount of analyte in the sample. The downstream detection zones can have binding substances of greater affinity for the analyte-labelled sbp member complex than the upstream detection zones to provide good discrimination as described earlier. FIG. 4 shows a representative example. Variations in both the binding affinities and the concentrations of the reagents immobilized on the multiple detection zones are used to control the kinetics of capture during liquid flow along the matrix:

1) Antibodies of varying affinity, e.g., $10^{-6}$, $10^{-7}$, $10^{-9}$, $10^{-10}$ and so on as determined by Scatchard analysis are used on different detection zones.

2) A high affinity antibody may generally be adjusted to have a lower affinity by chemical derivatization. For example, a small hapten may be conjugated to the antibody at varying ratios, 100:1, 10:1, 1:1, etc., to affect binding affinity (usually, increased derivatization results in decreased affinity). Alternatively, chemical substitution of the antibody may also affect affinity.

3) Antibodies to high frequency, intermediate frequency and rare frequency occurring antigen epitopes (all on the same antigen molecule) are used on separate capture zones to selectively partition antigens, labelled antigens or complexes thereof.

4) High affinity antibody is mixed in varying proportions with irrelevant antibody, e.g., high affinity mouse anti-analyte or anti-globulin mixed with normal mouse IgG.

5) Different ligand-receptor binding pair capture reagents of varying affinity, e.g., anti-mouse IgG and streptavidin-biotin as in FIG. 4. The arrays of binding substances immobilized on the various capture zones disclosed herein provide for the capture of the complexes that reach the detection zone as a function of analyte concentration. "Breakthrough" of a labelled species, usually an analyte-labelled sbp member complex, to a downstream zone only occurs when the analyte concentration exceeds a specific threshold value, thus allowing for precise correlation of the number of colored detection zones with analyte concentration. The binding reagent arrays of this invention, through choice of reagent and/or control of immobilized reagent quantity and/or concentration allow for 100% bound/free separation of the mixture of components formed during the assay as a function of sample analyte concentration or desired threshold level. Different barrier zones on multiple flow paths, each barrier zone selecting for a different threshold analyte level can be used. Alternatively, the same strip may employ different detection zones, where each detection zone behaves as a metering site, allowing the species being detected to "break through" to the next downstream zone only when analyte concentration exceeds (or falls below, for inverse read out assays) a desired threshold level.

The law of mass action, sample fluid flux, matrix flow size, matrix blocking methods, control of the antibody sbp member on the label and its spatial orientation, the concentration, purity and immunoreactivity of the binding reagent immobilized in the barrier or detection zones, along with other factors, affect the efficiency of the bound/free separation in the lateral flow format. Preferably, one uses a low level of purified antibody covalently bound to the label as labelling reagent and the antibody is spaced optimally for efficient analyte binding kinetics in the liquid phase. The antibody is preferably oriented such that the binding sites face outwards. The matrix is preferably a blocked nitrocellulose capable of non-bibulous flow. The labelling reagent usually rehydrates rapidly in the labelling zone and is maximally immunoreactive. The binding substance (usually analyte or analyte analog, e.g., antigen) in the barrier zone is typically of high purity and in an immunologically reactive form, preferably providing a single epitope for antibody binding.

This invention also provides devices as shown in FIG. 1 for quantitation of analytes using barrier zones on the capture zone. These devices are constructed with a sample receiving pad 12, a labelling zone 14 and a capture zone 16 as shown. In this particular embodiment, the most upstream capture line 16a is the barrier zone. The barrier zone has immobilized therein an sbp member complementary to the analyte or an analyte analog depending on the assay format being used. One skilled in the art will recognize that the barrier zone may be a multiplicity of capture lines or a line of varying width. The succeeding downstream capture lines 16b, 16c and so on are the detection zones which have immobilized therein a binding substance for the labelled analyte or the analyte-labelled sbp member complex respectively, depending on the assay format being used as described earlier. Additional barrier zones may be placed downstream of the first barrier zone 16a and spaced in between the detection zones 16b, 16c and so on to facilitate separation of the complex that has broken through. These additional barrier zones can be masked from view to simplify the readout. The pattern of signal on the detection zones can be correlated with analyte concentration as described earlier.

Figure 2:
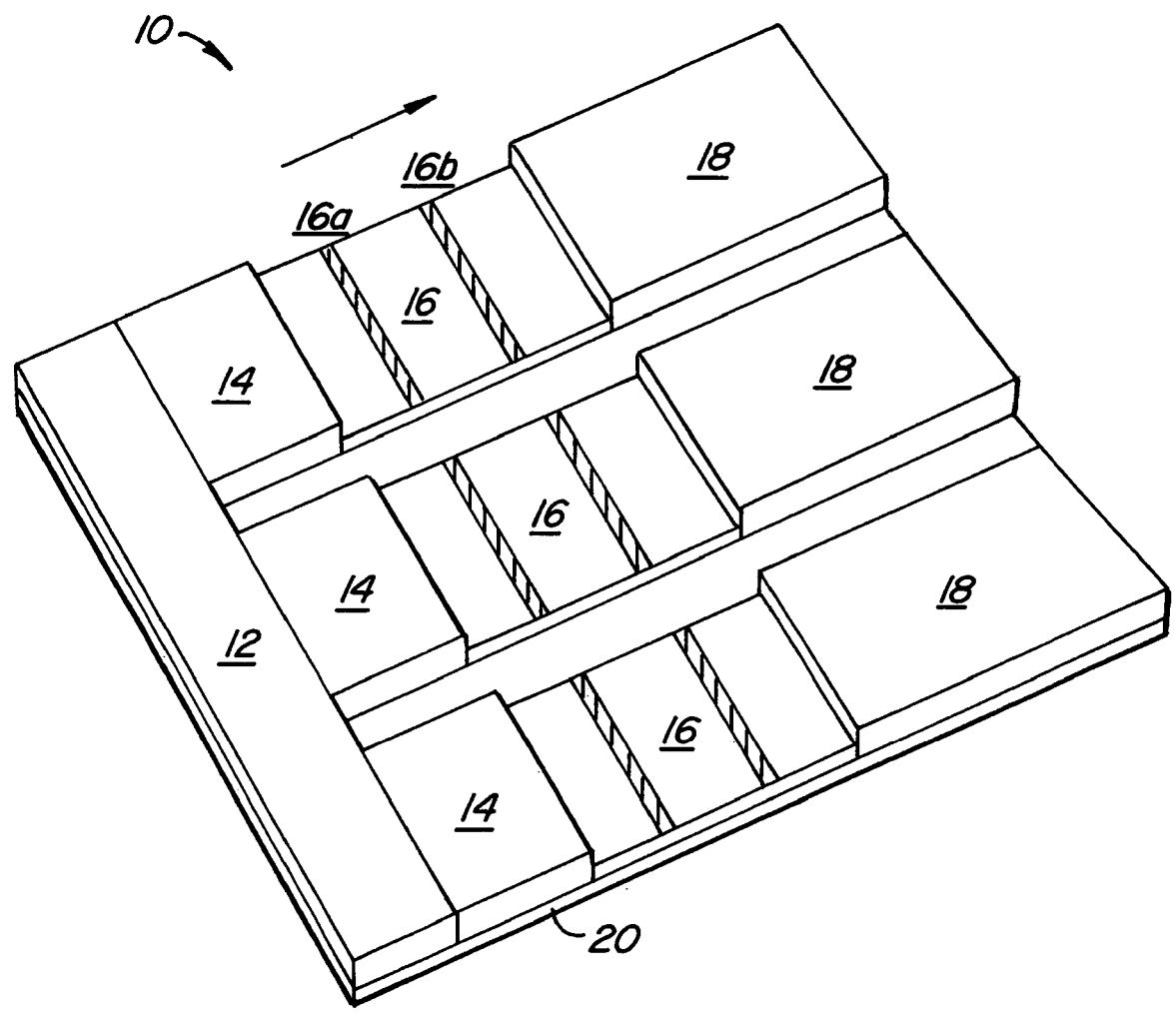
FIG. 2 shows a multiple flow path lateral flow assay device in which multiple flow paths emanate from a single sample receiving zone 12 with labelling zones 14 on the flow paths and intermediate barrier zones 16a of varying analyte analogue concentration on the different flow paths are placed upstream of the detection zones 16b.

One embodiment of the above format with barrier zones employs a device which has a multiplicity of separate matrices each defining a flow path fluidly isolated from the others emanating from a common sample receiving zone 12 as shown in FIG. 2. Each matrix comprises the following components in fluid flow contact arranged in downstream sequence as listed. (1) a labelling zone 14, (2) a capture zone 16, and optionally (3) an absorbent pad 18. The labelling zone 14 comprises an impregnated, freely diffusible labelling reagent, e.g., a labelled sbp member complementary to the analyte. The capture zone 16 has two capture lines. The first capture line 16a, the barrier zone, has immobilized therein an analyte analog. The nature, density and/or amount of analyte analog on the barrier zones of the different matrices varies, such that breakthrough of the labelled species being detected at the detection zone is a function of sample analyte concentration. In this context, breakthrough means that a detectable portion of a labelled species being detected flows through the barrier zone and is detected on the detection zone(s) when a threshold analyte concentration is exceeded. Typically, for a given barrier zone, this is a function of analyte concentration in the sample and the concentration of analyte needed for breakthrough to occur is referred to as the threshold concentration. Depending on the assay format being used, the threshold concentration can be set to a minimum or a maximum analyte concentration. Usually, barrier zones are set such that breakthrough occurs at that particular barrier zone when sample analyte concentration exceeds a particular level, i.e., above a minimum concentration. The labelled species that breaks through and is detected at the detection zone can be the labelling reagent itself or a complex containing the labelling reagent. For example, FIG. 2 shows a device with analyte analog on the barrier zones (16a) increasing in concentration from left to right. A second capture line, the detection zone 16b, is downstream of the first capture line and has an analyte analog immobilized therein which captures the labelled sbp member that breaks through the barrier zone 16a. The detection zone is unable to bind to the analyte-labelled sbp member complex.

The barrier zones are set at different analyte breakthrough thresholds on each separate matrix, by varying, for example, the concentration or binding affinity of the analyte analog immobilized therein. Analyte and free labelled sbp member bind to each other while the fluid sample flows towards the barrier zone. For a given concentration of analyte in the sample, a fixed amount of unbound labelled sbp member reaches each of the barrier zones on the different matrices. Color appears at those detection zones 16b which are downstream of those barrier zones whose breakthrough thresholds have been exceeded. However, as sample analyte increases, increasing amounts of the labelled sbp member are bound as analyte-labelled sbp member complex. In other words, less free labelled sbp member reaches the barrier zones as the sample analyte concentration increases. As a result, a decreasing number of barrier zones have their breakthrough concentrations exceeded and a fewer number of lines are observed on the detection zones thus allowing analyte quantitation. Therefore, when sample analyte is present at high concentration, color will appear at a fewer number of detection zones, i.e., those which are located downstream of the lower density barrier zones. Conversely, when sample analyte is present at lower concentrations, a greater amount of unbound labelled sbp member will reach each of the barrier zones and therefore color will appear on detection zones which are downstream of high density as well as low density barrier zones. As will be apparent, one can adjust the density of the analyte analog immobilized on the different barrier zones such that the pattern of appearance of signal on the detection zones can be correlated with analyte concentration.

In an alternate scenario, the detection zone 16b has immobilized therein a capture reagent which can bind the analyte-labelled sbp member complex which passes through the barrier zone. For example, this can occur when the labelling reagent is labelled mouse anti-analyte and the detection zone is goat anti-mouse IgG. As sample analyte concentration increases, increasing amounts of analyte-labelled anti-analyte form, pass through the barrier zone and are captured on the detection zone. A barrier zone with a low breakthrough threshold concentration, e.g, those with lower concentrations of analyte analog immobilized therein, will allow analyte-labelled anti-analyte to flow through at low sample analyte concentrations. Conversely, barrier zones with high breakthrough threshold concentrations will only allow analyte-labelled anti-analyte to flow through at high sample analyte concentrations. Therefore, at low sample analyte concentrations, color will appear on few or no detection zones, those being the ones downstream of the low breakthrough threshold barrier zones. At high sample analyte concentrations, color will appear on many more detection zones, the additional detection zones being those which are downstream of the high breakthrough threshold barrier zones, thus allowing quantitation of the sample.

Another variant of this invention with barrier zones and detection zones employs soluble unlabelled sbp member, such as an antibody, to vary the quantitation range of the assay. Soluble antibody can be used in a single lane essay or a multilane assay. In a single lane assay, the soluble antibody is used to bring the assay response into a linear quantitation range. In a multilane assay, where different concentrations of soluble antibody can be used, the soluble antibody can be used to affect the breakthrough threshold analyte concentrations. The soluble antibody may be premixed with the sample or impregnated into the sample receiving zone. This antibody binds to the antigen in the sample, thereby allowing one to control the sensitivity of the assay and/or the amount of analyte delivered to the labelling zone for binding to the labelled sbp member for subsequent reaction and separation. For a given level of antigen, the addition of soluble unlabelled antibody decreases or controls the amount of antigen available from the sample to bind to the labelled antibody and form an antigen-labelled antibody complex. Thus, the amount of antigen-labelled antibody complex formed is decreased, controlling or desensitizing the assay, allowing it to work in the concentration range in which the quantitation response is linear. In other words, the soluble antibody behaves as a "sink" which binds up a portion of the antigen thus effectively removing it from the immunoassay detection system. When sample fluid reaches the labelling zone, remaining free sample antigen, i.e., that is within the desired concentration range for the assay, can bind to labelled antibody. As the sample flows along the matrix and through the barrier zone, sample antigen competes with immobilized antigen on the barrier zone for the labelled antibody and the assay proceeds as described earlier. If sample antigen is present at a concentration above the threshold concentration as set by the barrier zone, antigen-labelled antibody complex breaks through to the detection zone, because the soluble sample antigen will effectively out-compete the bound antigen within the barrier zone. Immobilized antibody at the detection zone will then bind to and capture the antigen-labelled antibody complex at the second or capture zone, generating a positive signal. Because only antigen-labelled antibody complex breaks through the barrier zone, the immobilized antibody within the capture zone may be either an antibody specific for the antigen or alternatively, a nonspecific antiglobulin whivh will bind the antibody portion of the complex.

It is preferred that soluble antibody-analyte complex be retained in the sample receiving zone by immobilizing the free antibody directly to the matrix which makes up the sample receiving zone, or by having it immobilized on colorless latex particles which do not migrate into the labelling zone. If the soluble antibody-analyte complex is allowed to migrate into the detection zone, it might interfere with capture on the detection zones.

If the soluble antibody-analyte complex does indeed migrate into the detection zone(s), it is important that the sbp member on the detection zone not recognize the soluble analyte-antigen complex. This can be particularly troublesome where the same antibody is used as both the soluble antibody and the labeling antibody. This can be accomplished for example, by using a chimeric labeling reagent, i.e., comprised of an unrelated ligand that is conjugated to the labelled sbp member, e.g., antibody (which is complementary to the analyte), and providing a receptor to the unrelated ligand immobilized on the detection zone as detection reagent. By "unrelated ligand" is meant a ligand that is not a sbp member with the analyte or complements of the analyte. A variety of unrelated ligand-receptor pairs may be employed in this embodiment, including biotin-avidin/streptavidin, FITC-anti-FITC and the like.

When a receptor to the unrelated ligand is used as a capture reagent on the detection zone, only labelled complex, bearing the unrelated ligand will be bound to the detection zone. The soluble antibody-analyte complex, lacking the unrelated ligand, will not be retained by the detection zone and will flow through to the adsorbent pad.

Figure 3:
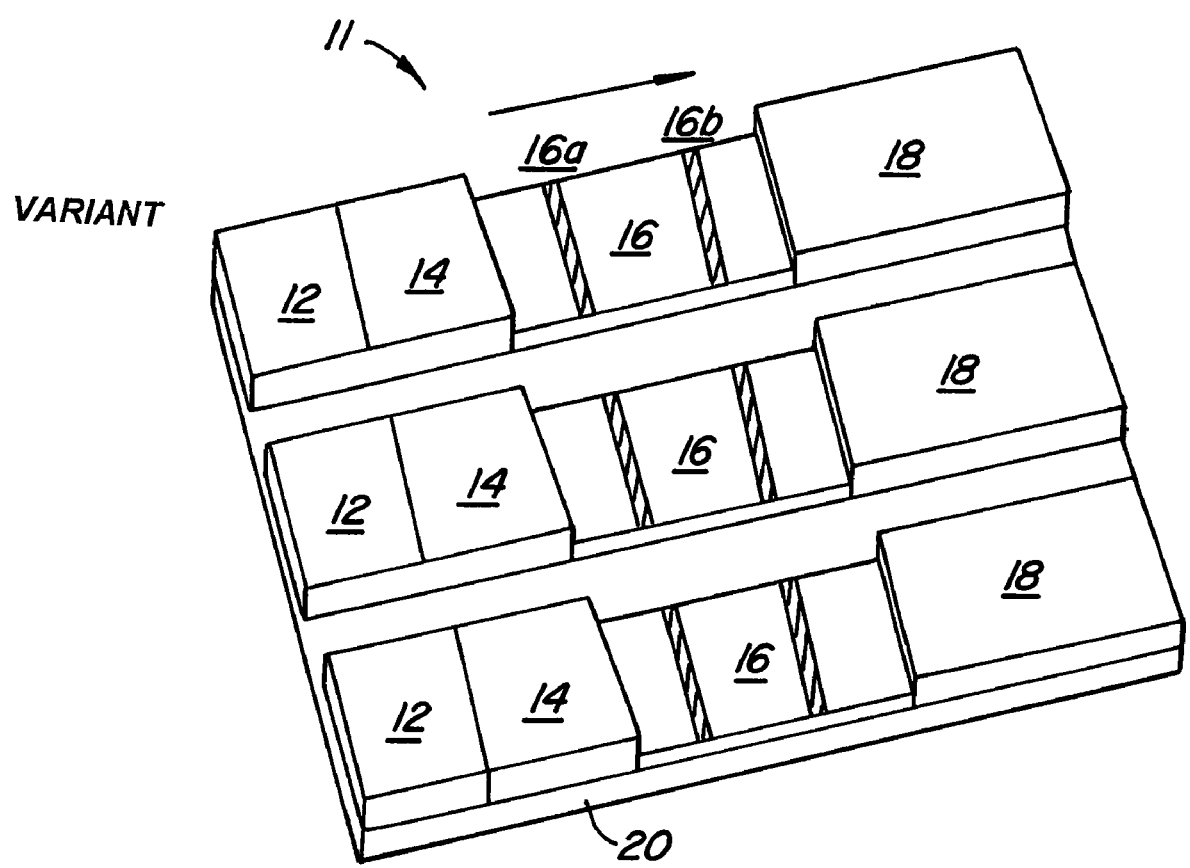
FIG. 3 shows a multiple flow path lateral flow assay device with multiple matrices in fluid flow isolation from each other, each matrix having a sample receiving pad 12 in which varying amounts of an sbp member for the analyte are diffusively bound, labelling zones 14, intermediate barrier zones 16a and detection zones 16b.

A format similar to the above, employing soluble antibody as a sink, may be used in a multi-flow path device, as illustrated in FIG. 3, in which each flow path utilizes a different concentration of soluble antibody. The device has a multiplicity of matrices each defining a separate flow path each in fluid flow isolation from the others. Each matrix comprises the following components arranged in downstream sequence as listed. (1) a sample receiving pad 12, (2) a labelling zone 14, (3) a capture zone 16 and optionally (4) an absorbent pad 18. With reference to FIG. 3, sample receiving pads 12 contain different amounts of impregnated, freely diffusible soluble antibody. Sample suspected of containing the analyte is added to the sample receiving pads 12 where it reacts with the soluble antibody to form an analyte-antibody complex. The sample then flows to the labelling zones 14 which contain impregnated freely diffusible labelled antibody. Free analyte binds to labelled antibody in the labelling zones. This mixture then flows to the capture zones 16. The capture zones 16 have two parallel capture lines, the first, a barrier zone 16a as described earlier, having immobilized thereon an analyte analog that is capable of binding 100% of the labelled antibody in the absence of free analyte, and the second, a detection zone 16b, which is downstream of the barrier zone, having immobilized thereon, an sbp member which can bind the analyte-labelled antibody complex only. The barrier zone will capture any free labelled antibody, while the downstream detection zone will capture the analyte-labelled antibody complex that exceeds the barrier zone threshold. Increasing amounts of soluble antibody on the discrete sample receiving pads 12 will "mop up" increasing amounts of analyte, resulting in decreasing amounts of analyte available to form analyte-labelled antibody complex in the label pad. Therefore, both soluble antibody concentration and barrier-zone breakthrough thresholds could be used to modulate the response on the detection zone of each flow path and facilitate quantitation. This is useful when concentration of analyte occurs over a wide dynamic range and dual modulation is needed to maintain stoichiometry. For a given analyte concentration in the sample, breaking through a barrier zone is more difficult for those barrier zones on flow paths containing a higher concentration of soluble antibody on their respective sample receiving pads. Therefore, at low analyte concentrations color will only appear on flow paths having low concentrations of soluble antibody. As analyte concentration increases, color will also appear on detection zones on flow paths having higher amounts of soluble antibody. As explained previously, the number of colored detection zones or the pattern of color on the detection zones after a predetermined time can be correlated with the analyte concentration in the sample. Table 11 shows the results with a multi-flow path device as in FIG. 3 using increasing amounts of soluble antibody on the sample receiving zones as one proceeds from left to right; fixed amounts of analyte analog (PDG-IgG) on the barrier zones and goat anti-mouse IgG on the detection zone.

Flow Matrix

The support matrix of the device may be capable of either bibulous or non-bibulous lateral flow. By "non-bibulous lateral flow" is meant liquid flow in which all of the dissolved or dispersed components of the liquid are carried at substantially equal rates and with relatively unimpaired flow, laterally through the membrane or matrix, as opposed to preferential retention of one or more components as would occur, e.g., in materials capable of adsorbing or imbibing one or more components. Bibulous flow is usually preferred. Matrices capable of such lateral flow are generally referred to herein as "lateral flow matrices."

A typical non-bibulous material suitable for use as a support matrix is high density polyethylene sheet material manufactured by Porex Technologies Corp. of Fairburn, Ga., USA. The sheet material has an open pore structure with a typical density, at 40% void volume, of 0.57 gm/cc and an average pore diameter of 1 to 250 micrometers, the average generally being from 3 to 100 micrometers. The optimum pore diameter for the membrane for use in the invention is about 10 to about 50 µm. The membranes typically are from about 1 mil to about 15 mils in thickness, typically in the range of from 5 or 10 mils, but may be up to 200 mils and thicker. The membrane may be backed by a generally water impervious layer, such as mylar. When employed, the backing is generally fastened to the membrane by an adhesive, such as 3M 444™ (3M Co., Minneapolis, Minn.) double-sided adhesive tape. Typically, a water impervious backing is used for membranes of low thickness. A wide variety of polymers may be used provided that they do not bind nonspecifically to the assay components and do not interfere with flow of the sample. Illustrative polymers include polyethylene, polypropylene, polystyrene and the like. Alternatively, the membrane may be self supporting. Other non-bibulous membranes, such as polyvinyl chloride, polyvinyl acetate, copolymers of vinyl acetate and vinyl chloride, polyamide, polycarbonate, polystyrene, and the like, can also be used.

Bibulous materials, such as untreated paper, cellulose blends, nitrocellulose, polyester, an acrylonitrile copolymer, rayon, glass fiber, and the like may also be employed as support matrix materials to provide either bibulous or non-bibulous flow. Especially preferred are microporous materials made from nitrocellulose, by which term is meant any nitric acid ester of cellulose. Thus suitable materials may include nitrocellulose in combination with carboxylic acid esters of cellulose. The pore size of nitrocellulose membranes may vary widely, but is preferably within 1 to 20 microns, preferably 8 to 15 microns. To provide non-bibulous flow, these materials may be treated with blocking agents that may block the forces which account for the bibulous nature of bibulous membranes. Suitable blocking agents include bovine serum albumin, methylated bovine serum albumin, whole animal serum, casein, and non-fat dry milk.

Typically, the support matrix will define a flow path. The flow path is generally axial, although other configurations are acceptable and may be preferred for some embodiments. For example, radial, multilane, tortuous or circular flow paths are particularly useful for test devices which can simultaneously detect the presence of multiple analytes in a sample.

The matrix may have to be activated in order to immobilize the specific binding pair member. Various methods may be employed based on the nature of the membrane and the particular binding pair member being employed. Generally when the membrane is nitrocellulose or a mixed nitrocellulose ester no special chemical linkage is required. For other materials, various other techniques such as activation by carbonyldiimidazole, glutaraldehyde, succinic acid, cyanogen bromide and the like may be employed. Alternatively, particles having an immobilized specific binding pair member may be used to immobilize the specific binding pair member on the capture zone. Exemplary of such particles are latex beads made of polystyrene, polyacrylates and polyacrylamides. The particles must be capable of nondiffusive attachment of the specific binding pair member by covalent or noncovalent binding. When the specific binding pair member is to be covalently bound a variety of particles containing functionalities such as carboxylic acids, aldehydes, amines, maleiimides, thiols, hydroxyls and the like may be used. The particles may be applied to the capture zone by a standard printing process including the use of electrostatic and laser controlled jets, and printing probe or type face. Alternatively, a suspension of the particles can be transferred to the capture zone by inscribing with a pen or microcapillary tube.

A bibulous absorbent zone is generally included in the devices of the present invention. The absorbent zone is located downstream from the capture zone. The absorbent zone is a means for removing excess sample and free dye or stained species other than the analyte of interest from the matrix of the device. Generally, the absorbent zone will consist of an absorbent material such as filter paper, a glass fiber filter, or the like. The absorbent can be a reversible or nonreversible dessicant which can remove all fluid from the matrix, thus "drying out" the strips and terminating the reaction by stopping flow, avoiding back flow of reagents or stopping binding to any of the capture, barrier or detection zones of the devices disclosed herein. This assists in providing sharp signals on the detection zones and avoids confusion which might be caused by signal appearing on a detection zone after the predetermined read time. It may also be used to drive the assay to completion, to assure unidirectional flow of sample, and separated but free immunoreagents.

The device may contain an end of assay indicator. The end of assay indicator may consist of a pH indicating reagent (such as bromocresol green) impregnated in the absorbent zone. Upon contact with the treated sample, a pH change occurs in the processed absorbent. This pH shift converts the pH indicator to a different color (for instance, bromcresol green may be converted from yellow to blue) which is seen in an observation window over the absorbent zone. This technology may also serve as an internal assay control. For example, a neutralized stained sample will convert the end of assay indicator from bright yellow to blue. If the neutralization is incomplete, the lower pH of the acidic sample solution will produce a green end color. An underneutralized sample may produce suspect results, the wrong color (green in this case) in the end of assay vent can serve as a signal that the assay may be comprised.

Labels

As described herein, the methods of the present invention typically utilize one or more labelled reagents. A variety of labeling methods can be used in the present methods, including colorimetric, chemiluminescent, fluorescent and other known labeling methods. The methods of the present invention will preferably employ labels which are directly visible. Such labels include but are not limited to particulate labels such as dyed latex beads, erythrocytes, liposomes, dyes sols, metallic and nonmetallic colloids, stained microorganisms and other such labels known to those skilled in the art. Non-particulate labels such as the target-specific antigen complexes described in U.S. patent application Ser. No. 08/408,441, filed Mar. 16, 1995, can also be used. Suitable labels such as colloidal metals, e.g. gold, and dye particles are disclosed in U.S. Pat. Nos. 4,313,734 and 4,373,932, both incorporated by reference. Non-metallic colloids, such as colloidal selenium, tellurium and sulfur are disclosed in U.S. Pat. No. 4,954,452, incorporated by reference. Dyed microorganisms as labels are disclosed in U.S. Pat. No. 5,424,193, EP 0 074 520 and British Patent No. GB 1,194,256, all incorporated by reference. Dyed latex particles are disclosed in U.S. Pat. No. 4,703,017, incorporated by reference.

The correlation between the visible intensity of accumulated label on the detection zones and analyte concentration in the sample may be made by comparison of the visible intensity to a reference standard. Optical detection devices may be programmed to automatically perform this comparison by means similar to that used by the Quidel Reflective Analyzer, Catalog No. QU0801 (Quidel Corp., San Diego, Calif.). Visual comparison is also possible by visual evaluation of the intensity and a color key such as used in the Quidel Total IgE Test Catalog No. 0701 (a multi-step ELISA assay). Densitometers and video image analyzers for performing this function are also known to those of skill in the art (*Immunocytochemistry: A Practical Approach*, ed. J. E. Beasely, IRL Press, (1993)). Typically, a video image analyzer comprises a digitizing tablet linked to a host computer. The matrix and capture zone are inspected by a microscope or other scanning device and the microscopic image is projected onto the digitizing tablet by a video camera. The computer analyzes the X,Y coordinates of the image to produce a digitized image. Such means are useful for performing high throughput automated screening of multiple samples. Thus, analyte concentration may be determined by the present invention.

If the dye used is a visible dye then the signal on the detection zone is visually discernible. Alternatively, if a fluorescent dye is used the accumulation of the label can be detected by employing a simple fluorescent detection means such as, for example, a hand held ultraviolet lamp (Mineralight Model UVGL (UVP Inc.)) or a fluorescent microscope (Diastar (Reichart Inc.)). Thus, a variety of detection methods are available to detect the accumulated label on the capture zone.

Kits

The present invention also provides kits comprising the devices described above for performing the methods disclosed herein with instructions for performing the method and interpreting the assay results. Typically, the instructions will include a chart or table which correlates the pattern of signal observed on the detection zone(s) with the analyte concentration in the sample.

The following examples are offered by way of illustration, not by way of limitation.

Abbreviations:
PBS—phosphate buffered saline
DEAE—Diethylaminoethyl
Tris—Tris(hydroxymethyl)aminomethane

EXAMPLES

Examples 1–3

Sandwich Assays for IgE

Preparation of Reagents

Preparation of Purified Mouse Monoclonal Anti-IgE

Anti-IgE was isolated from mouse ascites fluid at 0–4° C. by delipidation with sodium dextran sulfate and calcium chloride followed by ammonium sulfate treatment at 50% salt saturation and desalted on a G25 column into phosphate-buffered saline (pH 7.2; PBS). The anti-IgE antibodies were then further purified by DEAE ion-exchange chromatography. The ammonium sulfate fraction was applied to a column of DEAE cellulose (Whatman, DE-52). Purified anti-IgE was eluted with 0.04M sodium phosphate pH 8.0. Fractionation was monitored at 280 nm; fractions containing pure antibody were assessed by SDS PAGE analysis and pooled. The buffer was exchanged by gel chromatography on Sephadex G-25 (Pharmacia) equilibrated with 0.10 M sodium phosphate, pH 7.0. Finally, the antibody was concentrated by ultra filtration to 4.5 mg/ml and stored frozen at −20° C.

Biotinylation of Goat Anti-IgE

Affinity purified polyclonal goat anti-IgE (2.0 mg/ml, Kirkegaard & Perry, Inc.) was dissolved in 0.05M sodium bicarbonate, pH 8.5. N-Hydroxysuccinimido-biotin, 40 μl, 10 mg/ml in dimethylformamide, was added with stirring to the anti-IgE solution. The resulting clear solution was stirred for 3 hours at room temperature. Biotinylated goat anti-IgE was separated from unreacted biotin and dimethylformamide by desalting gel chromatography on PD-10 column (Pharmacia) packed with Sephadex G-25 equilibrated with 10 mM phosphate buffered 150 mM saline, pH 7.2, 0.02% sodium azide. The purified biotinylated anti-IgE was stored frozen at −20° C.

Preparation of Mouse Anti-IgE Coated and Goat Anti-IgE Coated Latex Microspheres Polystyrene latex microspheres, 0.50 ml, (0.51μ, Red, Polysciences, Inc.) were dispersed in 0.50 ml 0.05M tris buffer, pH 8.0 with 0.02% sodium azide, in a 1.5 ml Eppendorf conical polypropylene tube and sedimented by centrifugation on Eppendorf Microfuge. The supernatant was carefully removed and discarded. Either mouse anti-IgE, 0.50 ml, 0.71 mg/ml in Tris buffer, or goat anti-IgE, 0.50 ml, 2.4 mg/ml in Tris buffer (Kirkegaard & Perry, Inc.) was added and the pellet resuspended using a glass rod and vortex mixing. The suspension was rotated on an end-over-end rotator (SEPCO) for 24 hours at room temperature. The latex was pelleted by centrifugation. The supernatant was carefully removed and the pellet resuspended in 0.50 ml 10 mg/ml methylated bovine serum albumin in Tris buffer using a glass rod and vortex mixing. The suspension was rotated end-over-end on the rotator for 4 hours. The latex was pelleted by centrifugation for 2 minutes and the supernatant carefully removed. The pellet was resuspended in 0.50 ml 1 mg/ml methylated bovine serum albumin in Tris buffer using a glass rod and vortex mixing. The latex was washed twice more by centrifugation followed by resuspension. Finally, the pellet was suspended in 0.50 ml 1 mg/ml methylated bovine serum albumin in Tris buffer. Its latex concentration was adjusted to 1.0% solids by adding the appropriate amount of 1 mg/ml methylated bovine serum albumin after analyzing the solids content by spectroscopy at 450 nm. The suspension was stored at 2–8° C.

Preparation of Lateral Flow Assay Device

Lateral flow nonbibulous assay test strips were constructed according to the methodology contained in co-pending application Ser. No. 07/639,967. The test device (FIG. 1) includes three active zones and fourth absorbent zone which acts as a wick or sink to receive sample flow from the active zones. The active zones comprise a sample receiving zone 12, a labelling zone or intermediate zone 14, and a capture zone 16, as described below. Test strips were constructed as follows:

Preparation of Sample Receiving and Labelling Zones

The sample receiving zone and labelling zones were prepared from Sontara® 0–100 DuPont Orlon® spunlace fabric. The fabric was rendered nonbibulous by saturating with methylated bovine serum albumin (BSA). The sample receiving zone was prepared by treatment at 38 μl/cm² with a 10 mg/ml solution of the methylated BSA at room temperature for five minutes. The labelling zone was prepared by one of two methods dependent on the end usage of the test strips. For test strips used in "wet" assay formats, the labelling zone was prepared identically to sample receiving zone. For test strips used in "dry" reagent assay formats, the labelling zone was prepared by treatment at 38 μl/cm² with a suspension of antibody coated colored latex microspheres, diluted with 10 mg/ml methylated BSA in tris buffer to a concentration of 0.06% solids. The wet pads of Sontara® were then frozen at −70° C. for at least an hour. The Sontara® fabric was then lyophilized overnight on a Virtis Freezemobile. The sample receiving pad and the labelling zone pad were then cut into 10×4 mm rectangles with the spunlace fibers being parallel to the longer side of each pad.

Preparation of Capture Zone Membranes

Nitrocellulose having a pore size of 8 μm was affixed to an X-Y chart recorder, and capture bands were formed as spaced parallel lines of antibody, or streptavidin, or PDG-labeled IgG using a plotter pen operated in the manual mode. After air drying for 10 minutes at room temperature, the nitrocellulose membrane was placed into a tray containing blocking buffer (10 mg/ml BSA in the above Tris buffer) for 15 minutes at room temperature. The membrane was removed, blotted, allowed to air dry, and subsequently stored in a desiccator at room temperature until assembly of the device.

Assembly of the Device

A 20×4 mm strip of the capture zone membrane was affixed centrally to an adhesive transparency strip. The transparency strip was a 60×4 mm strip of overhead projection transparency film, made adhesive with double-sided adhesive tape. The labelling zone was then affixed next to the capture zone pad with a 1 mm overlap. The sample receiving zone was then affixed next to the labelling zone with a 1 mm overlap.

The device was then provided with an absorbent pad, which was a 20×4 mm rectangle of cellulose paper which was affixed to the distal end of the capture zone membrane with a 1 mm overlap.

Example 1

Direct Immobilization on Capture Zone

Capture zone membrane was prepared by placing three parallel capture bands of goat anti-IgE in tris buffer, 1.8 mg/ml, on nitrocellulose with 5 mm spacing between them using the X-Y chart recorder. Capture zone membrane, 20 mm wide, was cut with the three capture bands centered. Test strips were assembled for the "dry" reagent assay format from the capture zone membrane, sample receiving zone, and the labelling zone containing 0.06% latex microspheres coated with monoclonal mouse anti-IgE, 0.71 mg/ml. Aqueous reconstituted lyophilized horse serum samples, 40 µl, containing known quantities of human IgE, 0, 5, 20, 50, 200 IU/ml were placed on the sample receiving zone of the test strips. Time was measured in seconds to first visual appearance of colored latex bound on each of the three capture bands. Results are summarized in Table 1.

Example 2

Immobilization on Capture Zone Via Secondary Ligand

Capture zone membrane was prepared by placing three parallel capture bands of streptavidin in tris buffer, 6.0 mg/ml (Scripps Lab, Inc.) on nitrocellulose with 5 mm spacing between them using the X-Y chart recorder. After the lines had dried for 10 minutes, biotinylated goat anti-IgE in tris buffer, 1.5 mg/ml, was placed in three parallel bands directly on top of the three dried streptavidin bands. Capture zone membrane, 20 mm wide, was cut with the three capture bands centered. Test strips were assembled for the "dry" reagent assay format from the capture zone, and labelling zone containing 0.06% latex microspheres coated with monoclonal mouse anti-IgE, 0.71 mg/ml. Aqueous reconstituted lyophilized horse serum samples, 40 µl, containing known quantities of human IgE, 0, 5, 20, 50, 200 IU/ml were placed on the sample receiving zone of the test strips. Time was measured in seconds to first visual appearance of colored latex bound on each of the three capture bands. Results are summarized in Table 2.

Example 3

Reversal of Capture Zone and Labelled Reagent

Capture zone membrane was prepared by placing three parallel capture bands of monoclonal mouse anti-IgE in Tris buffer, 0.60 mg/ml, on nitrocellulose with 5 mm spacing between them using the X-Y chart recorder. Capture zone membrane, 20 mm wide, was cut with the three capture bands centered. Test strips were assembled for the "dry" reagent assay format from the capture zone membrane, sample receiving zone, and the labelling zone containing 0.06% latex microspheres coated with goat anti-IgE, 2.4 mg/ml. Aqueous reconstituted lyophilized horse serum samples, 40 µl, containing known quantities of human IgE, 0, 5, 20, 50, 200 IU/ml were placed on the sample receiving zone of the test strips. Time was measured in seconds to first visual appearance of colored latex bound on each of the three capture bands. Results are summarized in Table 3.

TABLE 1

| Visual Call of Number | IgE Concentration in the Assay (I.U./ml) | | | | |
| --- | --- | --- | --- | --- | --- |
| of Lines at | 0 | 5 | 20 | 50 | 200 |
| 1 min | − | − | − | + | ++ |
| 2 min | − | − | − | ++ | +++ |
| 3 min | − | − | ++ | +++ | +++ |
| 6 min | − | ++ | +++ | +++ | +++ |

− 0 visible lines
+ 1 visible line
++ 2 visible lines
+++ 3 visible lines

TABLE 2

| Visual Call of Number | IgE Concentration in the Assay (I.U./ml) | | | | |
| --- | --- | --- | --- | --- | --- |
| of Lines at | 0 | 5 | 20 | 50 | 200 |
| 1 min | − | − | − | − | ++ |
| 3 min | − | − | − | ++ | +++ |
| 5 min | − | − | + | ++ | +++ |
| 10 min | − | + | +++ | +++ | +++ |

− 0 visible lines
+ 1 visible line
++ 2 visible lines
+++ 3 visible lines

TABLE 3

| Visual Call of Number | IgE Concentration in the Assay (I.U./ml) | | | | |
| --- | --- | --- | --- | --- | --- |
| of Lines at | 0 | 5 | 20 | 50 | 200 |
| 1 min | − | − | + | + | ++ |
| 2 min | − | + | ++ | ++ | ++ |
| 3 min | − | ++ | ++ | +++ | +++ |
| 4 min | − | +++ | +++ | +++ | +++ |

− 0 visible lines
+ 1 visible line
++ 2 visible lines
+++ 3 visible lines

Examples 4–5

Competitive Assays with Antianalyte Capture Zone

Biotinylation of Mouse Monoclonal Anti-Pregnanediol Gluconoride (PDG)

Protein A purified mouse anti-PDG, 1.0 mg/ml, was dissolved in 10 mM sodium phosphate 150 mM sodium chloride pH 7.2, 0.02% sodium azide (PBS). N-Hydroxysuccinimide-LC-biotin, 37 µl, 10 mg/ml in dimethylformamide, was added with stirring to the anti-PDG solution. The resulting clear solution was stirred for 3 hours at 25° C. Biotinylated goat anti-PDG was separated from unreacted biotin and dimethylformamide by gel chromatography on PD-10 column (Pharmacia) packed with Sephadex G-25 equilibrated with PBS. The purified biotinylated anti-PDG was stored frozen at −20° C.

Preparation of Pregnanediol Glucuronide Sulfo-N-hydroxysuccinimide Ester in Dimethylformamide Pregnanediol glucuronide, 11.5 mg (Sigma), 1-Ethyl-3 (3-dimethylaminopropyl)-carbodiimide (Sigma), 8.8 mg, and Sulfo-N-hydroxysuccinimide (Pierce), 5.8 mg were placed in a tightly stoppered test tube with 1150 µl anhydrous dimethylformamide and stirred with a flea-size magnetic stir bar at 18–25° C. After approximately one hour, the solids had completely dissolved. Stirring was continued for a total of 17 hours.

Conjugation of Pregnanediol Glucuronide to Bovine Serum Albumin (PDG-BSA Conjugate)

Bovine serum albumin, 40 mg, (Armour) was dissolved in 3.96 ml 0.10 M sodium bicarbonate sodium carbonate buffer, pH 9.0, and chilled in ice water. The dimethylformamide solution of PDG sulfo-N-hydroxysuccinimide ester, 848 mg, was added slowly with rapid stirring over 10 minutes to give an opalescent solution. The solution was incubated at 18–25° C. for 6.5 hours. It was them applied to a 40 cm$^3$ column containing Sephadex G-25 (Pharmacia) equilibrated with PBS buffer to separate the conjugated protein from unconjugated PDG, dimethylformamide, and reaction products. The conjugate was stored frozen at −20° C.

Preparation of PDG-BSA Conjugate Coated Latex Microspheres

Polystyrene latex microspheres, 0.50 ml, (0.51µ, Red, Polysciences, Inc.) were dispersed in 0.40 ml 25 mM tris buffer, pH 8.0 with 0.02% sodium azide, in a 1.5 ml Eppendorf conical polypropylene tube. PDG-BSA conjugate, 95.6 µl, 5.23 mg/ml, was added and the suspension was rotated on an end-over-end rotator (SEPCO) for 24 hours at room temperature. The latex was pelleted by centrifugation for 2 minutes. Supernatant was carefully removed with P-1000 Pipetman and the pellet resuspended in 1.00 ml 10 mg/ml methylated bovine serum albumin in tris buffer using a glass rod and vortex mixing. The suspension was rotated end-over-end on the rotator for 4 hours. The latex was pelleted by centrifugation for 2 minutes and the supernatant carefully removed with P-1000 Pipetman. The pellet was resuspended in 0.90 ml 10 mg/ml methylated bovine serum albumin in Tris buffer using a glass rod and vortex mixing. Its latex concentration was adjusted to 1.0% solids by adding the appropriate amount of 10 mg/ml methylated bovine serum albumin after analyzing the solids content by spectroscopy at 450 nm. The suspension was stored at 4–8° C.

Periodate Activation of Paper

Whatman #31 ET paper, 6"×11", was placed in a stainless steel tray and immersed in sodium periodate solution, 0.05 M, 267 ml. It was agitated gently on horizontal rotator for 45 minutes at room temperature. The sodium periodate solution was decanted and the paper washed with 2×267 ml deionized water for 5 minutes with each volume. The paper was then washed with ethylene glycol sodium carbonate buffer, pH 9.5, for 30 minutes at room temperature. After decanting the buffer, the paper was washed with 2×267 ml portions of deionized water for 5 minutes per wash. The paper was immediately used to couple avidin or streptavidin without allowing it to dry.

Avidin and Streptavidin Coupled Paper

Two pieces were cut from the wet periodate activated paper, 3"×6.5". Each was placed in a 6"×8" plastic tray. Avidin, 0.53 mg/ml, 100 ml, in coupling buffer, pH 8.3 was added to the periodate paper in one tray and streptavidin, 0.10 mg/ml, 100 ml, in coupling buffer was added to the periodate paper in the other tray. The trays were gently agitated on a horizontal rotating table for 22 hours at 4° C. The coupling solutions were decanted and each paper was washed with 2×20 ml portions of PBS buffer for 5 minutes per wash. Sodium borohydride, 0.10 M, 265 ml, was added to each tray and the trays were gently agitated on the horizontal rotating table for one hour at room temperature. The sodium borohydride solution was decanted and the papers were washed twice with 200 ml PBS buffer each for 5 minutes per wash. The PBS was decanted and 0.05M ethanolamine containing 1 mg/ml BSA, pH 8.1, 267 ml per tray, was added and the trays were gently agitated on the horizontal rotating table for one hour at room temperature. Ethanolamine buffer was decanted and the papers were washed alternately with coupling buffer, pH 8.3 and sodium acetate, pH 4.5, 200 ml per tray for a total of two washes with each buffer. Washing was continued with two 200 ml portions of PBS for 5 minutes per wash. Polyvinyl alcohol solution was added and the trays were gently agitated for 30 minutes on the horizontal rotating table. The papers were removed and blotted dry with paper towels. They were lyophilized for 16 hours at room temperature, and then stored in a dry room.

Coating Avidin-Paper and Streptavidin-Paper with Biotinylated Mouse Monoclonal Pregnanediol Glucuronide Biotinylated anti-pregnanediol glucuronide, 0.05 mg/ml, 30 ml, in PBS buffer was added to a polypropylene 7.5×11 cm tray containing 7×7.8 cm pieces of avidin-paper and streptavidin-paper. The tray was gently agitated at room temperature on the horizontal rotating table for 4 hours. The biotinylated anti-PDG solution was decanted and the papers treated successively as follows with 50 ml portions of the same buffers used to prepare the avidin-paper and streptavidin-paper: coupling buffer, 1 minute; acetate buffer, 1 minute; washing repeated with the same two buffers; washed twice with PBS, 5 minutes each; and polyvinyl alcohol solution, 30 minutes. The papers were blotted dry and lyophilized 17 hours at room temperature, then stored in a dry room.

Example 4

Biotinylated mouse monoclonal anti-pregnanediol glucuronide-streptavidin-paper was cut into strips, 3×85 mm. To one end of each strip was applied 200 µl of a urine test sample containing PDG-BSA-coated colored latex microspheres. Test samples containing known quantities of PDG and PDG-BSA coated latex microspheres were prepared by mixing 95 µl deionized water, 20 µl of a 10× concentrate of PBS, 20 µl of 10 mM 8-aniline-1-naphthalene sulfonic acid, ammonium salt (Aldrich), 20 µl of 250 mg/ml Ficoll 400 (Sigma), 10 µl male urine, 20 µl 100 mg/ml methylated BSA in Tris buffer, 5 µl PDG in 20% methanol/10 mg/ml methylated BSA, and 10 µl of PDG-BSA conjugate coated red latex microspheres, 1% solids. The liquid was allowed to flow along the strip to a distance of 72 mm. The flow distance of the red latex was measured with a ruler. Results are summarized in Table 4.

Example 5

Biotinylated mouse monoclonal anti-pregnanediol glucuronide-avidin-paper was cut into strips, 3×75 mm. To one end of each strip was applied 200 μl of a urine test sample containing PDG-BSA-coated colored latex microspheres. Test samples containing known quantities of PDG and PDG-BSA coated latex microspheres were prepared by mixing 70 μl deionized water, 20 μl of a 10× concentrate of PBS, 20 μl of 10 mM 8-aniline-1-naphthalene sulfonic acid, ammonium salt (Aldrich), 30 μl of 250 mg/ml Ficoll 400 (Sigma), 10 μl male urine, 20 μl 100 mg/ml methylated BSA in Tris buffer, 5 μl PDG in 20% methanol/10 mg/ml methylated BSA, and 10 μl of PDG-BSA conjugate coated red latex microspheres, 1% solids. The liquid was allowed to flow along the strip to a distance of 65 mm. Flow distance of the red latex was measured with a ruler. Results are summarized in Table 5.

TABLE 4

| PDG Concentration in the Assay (μg/ml) | Colored Latex Flow Distance (mm) | Difference of Flow Distance Between PDG Positive Sample and PDG Negative Sample (mm) | Liquid Migration Distance (mm) |
| --- | --- | --- | --- |
| 0 | 36 | 0 | 72 |
| 2 | 58 | 22 | 72 |
| 50 | 66 | 30 | 72 |

TABLE 5

| PDG Concentration in the Assay (μg/ml) | Colored Latex Flow Distance (mm) | Difference of Flow Distance Between PDG Positive Sample and PDG Negative Sample (mm) | Liquid Migration Distance (mm) |
| --- | --- | --- | --- |
| 0 | 35 | 0 | 65 |
| 50 | 47 | 12 | 65 |

Examples 6–9

Single Lane Lateral Flow Test Devices with Multiple Anti-Analyte or Multiple Analyte Capture Lines: PDG Assay Conjugation of Pregnanediol Glucuronide to Bovine IgG (PDG-IgG Conjugate)

Bovine IgG, 30 mg, (Sigma) was dissolved in 3.0 ml 0.10 M sodium bicarbonate sodium carbonate buffer, pH 9.0, and chilled in ice water. The dimethylformamide solution of PDG sulfo-N-hydroxysuccinimide ester, 300 μl, was added slowly with rapid stirring over 10 minutes to give an opalescent solution. The solution was incubated at 18–25° C. for 3 hours. It was them applied to a 25 cm³ column containing Sephadex G-25 (Pharmacia) equilibrated with PBS buffer to separate the conjugated protein from unconjugated PDG, dimethylformamide, and reaction products. The conjugate was stored frozen at −20° C.

Preparation of PDG-IgG Conjugate Coated Latex Microsphere

Polystyrene latex microspheres, 0.125 ml, (0.44μ, Red, Bangs) were dispersed in 0.793 ml 25 mM Tris buffer, pH 8.0 with 0.02% sodium azide, in a 1.5 ml Eppendorf conical polypropylene tube. PDG-IgG conjugate, 82 μl, 6.07 mg/ml, was added and the suspension was rotated on an end-over-end rotator (SEPCO) for 18 hours at room temperature. The latex was pelleted by centrifugation for 3 minutes. Supernatant was carefully removed and the pellet resuspended in 1.00 ml 10 mg/ml methylated bovine serum albumin in tris buffer using a glass rod and vortex mixing. The suspension was rotated end-over-end on the rotator for 4 hours. The latex was pelleted by centrifugation for 2 minutes and the supernatant carefully removed and the pellet was resuspended in 0.90 ml 10 mg/ml methylated bovine serum albumin in Tris buffer using a glass rod and vortex mixing. Its latex concentration was adjusted to 1.0% solids by adding the appropriate amount of 10 mg/ml methylated bovine serum albumin after analyzing the solids content by spectroscopy at 450 nm. The suspension was stored at 4–8° C.

Preparation of Mouse Monoclonal Anti-PDG Coated Latex

Polystyrene latex microspheres, 0.125 ml, (0.44μ, Red, Bangs) were dispersed in 0.751 ml 25 mM Tris buffer, pH 8.0 with 0.02% sodium azide, in a 1.5 ml Eppendorf conical polypropylene tube. Mouse monoclonal anti-PDG, 124 μl, 4.02 mg/ml, was added and the suspension was rotated on an end-over-end rotator (SEPCO) for 18 hours at room temperature. The latex was pelleted by centrifugation for 3 minutes. The supernatant was carefully removed with P-1000 Pipetman and the pellet resuspended in 1.00 ml 10 mg/ml methylated bovine serum albumin in Tris buffer using a glass rod and vortex mixing. The suspension was rotated end-over-end on the rotator for 4 hours. The latex was pelleted by centrifugation for 3 minutes and the supernatant carefully removed and the pellet was resuspended in 0.90 ml 10 mg/ml methylated bovine serum albumin in tris buffer using a glass rod and vortex mixing. Its latex concentration was adjusted to 1.0% solids by adding the appropriate amount of 10 mg/ml methylated bovine serum albumin after analyzing the solids content by spectroscopy at 450 nm. The suspension was stored at 4–8° C.

Example 6

Capture zone membrane was prepared by placing four parallel capture bands of mouse monoclonal anti-PDG, 1.0 mg/ml on nitrocellulose with 3 mm spacing between them using the X-Y chart recorder. The membrane was cut 20 mm wide with the four capture bands centered. Test strips were assembled for the wet assay format from the capture zone membrane, sample receiving zone, and an intermediate zone identical to sample receiving zone. Test solutions, 100 μl, containing known concentrations of PDG, were prepared by mixing 81.5 μl male urine, 10 μl PDG sample, 6 μl Ficoll, 250 mg/ml and 2.5 μl red latex microspheres coated with PDG-IgG conjugate, 1% solids. Each test solution, 40 μl, was applied to the sample receiving zone of a test strip. Time in seconds was recorded for appearance of first visually detectable red latex at each of the test bands for increasing concentrations of PDG in the test solutions. A summary of the test results appears in Table 6.

Example 7

Capture zone membrane was prepared by placing seven parallel capture bands of mouse monoclonal anti-PDG, 4.0 mg/ml on nitrocellulose with 5 mm spacing between them using the X-Y chart recorder. The membrane was cut 5 cm wide with the seven capture bands centered. Test strips were assembled for the wet assay format from the capture zone membrane, sample receiving zone, and an intermediate zone identical to sample receiving zone. Test solutions, 100 μl containing known concentrations of PDG were prepared by mixing 85 μl male urine, 10 μl PDG sample and 6 μl red latex microspheres coated with PDG-IgG conjugate, 1% solids. Each test solution, 60 μl, was applied to the sample receiving zone of a test strip. Time in seconds was recorded for appearance of first visually detectable red latex at each of the test bands for increasing concentrations of PDG in the test solutions. A summary of the test results appears in Table 7.

Example 8

Capture zone membrane was prepared by placing seven parallel capture bands of PDG-IgG conjugate, 4.0 mg/ml on nitrocellulose with 5 mm spacing between them using the X-Y chart recorder. The membrane was cut 5 cm wide with the seven capture bands centered. Test strips were assembled for the wet assay format from the capture zone membrane, sample receiving zone, and an intermediate zone identical to sample receiving zone. Test solutions, 100 μl containing known concentrations of PDG were prepared by mixing 81.5 μl male urine, 10 μl PDG sample, 6 μl Ficoll, 250 mg/ml and 2.5 μl red latex microspheres coated with mouse monoclonal anti-PDG, 1% solids. Each test solution, 60 μl, was applied to the sample receiving zone of a test strip. Time in seconds was recorded for appearance of first visually detectable red latex at each of the test bands for increasing concentrations of PDG in the test solutions. A summary of the test results appears in Table 8.

Example 9

Capture zone membrane was prepared by placing seven parallel capture bands of PDG-IgG conjugate, 4.0 mg/ml on nitrocellulose with 5 mm spacing between them using the X-Y chart recorder. The membrane was cut 5 cm wide with the seven capture bands centered. Test strips were assembled for the wet assay format from the capture zone membrane, sample receiving zone, and an intermediate zone identical to sample receiving zone. Test solutions, 100 μl containing known concentrations of PDG were prepared by mixing 85 μl male urine, 10 μl PDG sample and 5 μl red latex microspheres coated with mouse monoclonal anti-PDG, 1% solids. Each test solution, 60 μl, was applied to the sample receiving zone of a test strip. Time in seconds was recorded for appearance of first visually detectable red latex at each of the test bands for increasing concentrations of PDG in the test solutions. A summary of the test results appears in Table 9.

TABLE 6

| Visual Call of Number of Lines at | PDG Concentration in the Assay (μg/ml) | | | | | |
|---|---|---|---|---|---|---|
| | 0 | 5 | 10 | 20 | 50 | 100 |
| 0.2 min | + | + | + | + | + | + |
| 2 min | + | + | + | ++ | ++ | ++ |
| 3 min | + | + | ++ | ++ | ++ | ++ |
| 4 min | + | ++ | ++ | ++ | ++ | ++ |
| 10 min | + | ++ | ++ | ++ | ++ | +++ |
| >20 min (dry) | + | ++ | ++ | ++ | +++ | +++ |

+ 1 visible line
++ 2 visible lines
+++ 3 visible lines

TABLE 7

| Visual Call of Number of Lines at | PDG Concentration in the Assay (μg/ml) | | | |
|---|---|---|---|---|
| | 0 | 5 | 10 | 25 |
| 0.2 min | + | + | + | + |
| 2 min | + | + | + | ++ |
| 4 min | ++ | ++ | ++ | +++ |
| 6 min | +++ | +++ | +++ | +++ |
| >20 min | +++ | +++ | ++++ | +++++ |

+ 1 visible line
++ 2 visible lines
+++ 3 visible lines
++++ 4 visible lines
+++++ 5 visible lines

TABLE 8

| Visual Call of Number of Lines at | PDG Concentration in the Assay (μg/ml) | | |
|---|---|---|---|
| | 0 | 5 | 10 |
| 1 min | + | + | + |
| 4 min | + | ++ | ++ |
| >20 min (dry) | ++ | ++ | +++ |

+ 1 visible line
++ 2 visible lines
+++ 3 visible lines

TABLE 9

| Visual Call of Number of Lines at | PDG Concentration in the Assay (μg/ml) | |
|---|---|---|
| | 0 | 10 |
| 0.5 min | + | + |
| 1 min | ++ | ++ |
| 2 min | +++ | +++ |
| >20 min (dry) | +++++ | ++++++ |

+ 1 visible line
++ 2 visible lines
+++ 3 visible lines
+++++ 5 visible lines
++++++ 6 visible lines Multiple Lane Lateral Flow Test Devices General Description Test devices containing multiple individual lateral flow development lanes, useful for semi-quantitative, visual detection of an analyte, are depicted in FIG. 2 and FIG. 3. Each lane of the devices is designed to detect as a positive visual result, the analyte at concentrations above a given set cut-off concentration. The set cut-off concentrations increase from lane to lane from left to right. The number of positive lanes provides a semi-quantitative indication of analyte concentration in the sample. One device, FIG. 2, contains a sample receiving zone 12 to receive sample and disseminate it to each of the lateral flow lanes. The other device, FIG. 3, contains separate sample receiving zones, one for each lateral flow lane. Analyte cut-off concentrations were established in one of two ways: (1) by increasing from lane to lane from left to right the amount of PDG-IgG conjugate, or in the reverse scenario, the amount of antiglobulin, applied to the first capture line (Example 10 and FIG. 2), or (2) by supplementing the sample zone 12 with increasing amounts of anti-PDG antibody from lane to lane from left to right (Example 11 and FIG. 3).

Preparation of Three-Lane Lateral Flow Assay Device

The test devices (FIG. 2 and FIG. 3) include three active zones and fourth absorbent zone which acts as a wick or sink to receive sample flow from the active zones. The active zones comprise a sample receiving and disseminating zone 12 (FIG. 2) or three separate sample receiving zones 12 (FIG. 3), intermediate zones 14, and capture zones 16, and absorbent pads 18 as described below.

Test strips were constructed as follows:

Preparation of Sample Receiving and Disseminating Zone

The sample receiving and disseminating zone (FIG. 2) or sample receiving zones (FIG. 3) were prepared from Sontara® 0–100 in an identical procedure to that used for the sample receiving zone of the Lateral Flow Assay Device (FIG. 1) Pads, 10×14 mm rectangles, were cut with the spunlace fibers being parallel to the longer side of each pad (FIG. 2). Pads, 10×4 mm rectangles were cut with the spunlace fibers being parallel to the longer side of each pad (FIG. 3).

Preparation of the Intermediate Labelling Zone and Capture Zone Membrane

Intermediate zone and capture zone membrane were prepared identically to those used for the Lateral Flow Assay Device used in the dry reagent assay formats (FIG. 1).

Assembly of the Device

Three 20×4 mm strips of the capture zone membranes were affixed centrally to a 60×14 mm adhesive transparency film strip. The longer dimension of the capture zone membranes was placed parallel to the longer dimension of the transparency film strip with 1 mm gaps between the three membranes. The strip of transparency film was made adhesive with double-sided adhesive tape. Three 10×4 mm intermediate labelling zones were then affixed next to the three capture zones each with a 1 mm overlap. The 14×10 mm sample receiving and disseminating zone was then affixed next to the intermediate zones with its longer dimension perpendicular to the longer dimension of the transparency strip and with a 1 mm overlap of each of the three intermediate labelling zones (Device of FIG. 2) or affix the individual sample receiving zones with 1 mm overlaps with the three intermediate zones (Device of FIG. 3). The devices were then provided with three absorbent pads, which were 20×4 mm rectangles of cellulose paper which were affixed to the distill end of the three capture zone membranes each with a 1 mm overlap.

Example 10

PDG Assay Using Varying Barrier Zone Density

Three capture zone membranes were prepared by placing parallel capture bands of PDG-IgG conjugate, 0.25 mg/ml and goat anti-mouse IgG 0.25 mg/ml, on one piece of nitrocellulose with 5 mm spacing between them, 1.0 mg/ml PDG-IgG and 0.25 mg/ml goat anti-mouse IgG, on a second piece of nitrocellulose with 5 mm spacing between them, and 4.0 mg/ml PDG-IgG and 0.25 mg/ml goat anti-mouse IgG on a third piece of nitrocellulose with 5 mm spacing between them using an X-Y chart recorder. The varying PDG-IgG bands are the barrier zones and the constant goat anti-mouse IgG bands are the detection zones. The membranes were cut 20 mm wide with the capture bands centered. Three-lane test devices were assembled for the dry assay format from the three capture membranes, from three intermediate labelling zones containing latex label (mouse anti-PDG on red latex), and from a single sample receiving and disseminating zone.

Test solutions, 200 μl, containing known concentrations of PDG, were prepared by mixing 180 μl male urine and 20 μl PDG sample. A sample of each test solution, 120 μl, was applied to the sample receiving and disseminating zone of a device. Time in seconds was recorded for appearance of first visually detectable red latex at each of the detection zones on each of the three lanes. A summary of the test results appears in Table 10.

Example 11

PDG Assay Using Varying Soluble Antibody on Discrete Sample Pads

Capture zone membrane 16 was prepared by placing two parallel capture bands of PDG-IgG conjugate, 1.0 mg/ml (BARRIER ZONE 16*a*), and goat anti-mouse IgG, 0.25 mg/ml (DETECTION ZONE 16*b*), on nitrocellulose with 5 mm spacing between them using an X-Y chart recorder. The membranes were cut 20 mm wide with the capture bands centered. Three SAMPLE RECEIVING PADS 12 were prepared for the three lanes containing 50 μg/ml, 150 μg/ml and 450 μg/ml mouse monoclonal anti-PDG in 10 μg/ml methylated BSA in Tris buffer lyophilized into Sontara fabric. Three-lane test devices were assembled for the dry assay format from the three identical capture membranes 16, from the three sample receiving pads 12 containing 50 μg/ml, 150 μg/ml and 450 μg/ml anti-PDG, and from three intermediate labelling zones 16 containing latex label (mouse anti-PDG on red latex). The strips were assembled into a multilane device as described in Example 10, except that the sample receiving pads were in fluid isolation from each other.

Test solutions, 200 μl, containing known concentrations of PDG, were prepared by mixing 180 μl male urine and 20 μl PDG sample. Aliquots, 40 μL each, of the test solution were applied to each of the sample receiving pads of each test strip of the device. Time in seconds was recorded for appearance of first visually detectable red latex at each of the detection zones on each of the three lanes. A summary of the test results appears in Table 11.

TABLE 10

| | PDG Concentration in the Assay (μg/ml) | | | | | | |
|---|---|---|---|---|---|---|---|
| | 0 | 2 | 6 | 8 | 12 | 15 | 25 |
| Visual Call of Color on Second Line of Each Lane After 5 min. | −−− | −−− | +−− | +−− | ++− | ++− | +++ |

− no visible line in the lane
+ visible line in the lane

TABLE 11

| | PDG Concentration in the Assay (μg/ml) | | | | | |
|---|---|---|---|---|---|---|
| | 0 | 2 | 6 | 8 | 12 | 15 | 25 |
| Visual Call of Color on Second Line of Each Lane After 5 min. | --- | --- | +-- | +-- | ++- | ++- | +++ |

− no visible line in the lane
+ visible line in the lane

Examples 12–14

Single Lane Lateral Flow Test Devices with Barrier Zones and Detection Zones

Example 12

HCG Assay

This assay employed a device as shown in FIG. 1 with five lines of hCG-rabbit IgG (at 1 mg/ml) (BARRIER ZONE 16a) and one line of goat anti-mouse IgG ($F_c$) (affinity-purified, at 2.4 mg/mL) (DETECTION ZONE 16b) coated onto nitrocellulose in the capture zone 16. Anti-hCG dyed latex microspheres were prepared analogously to the anti-IgE microspheres and PDG-BSA microspheres used in Examples 1–3 and 4–5. The anti-HCG microspheres were first mixed with hCG samples at different concentrations. 11,490, 22,977, 45,953, 91,906, 183,812, 229,705, 306,353, 459,530, and 9,190,600 mIU/mL, and then loaded onto sample pad 12 and allowed to run through the intermediate zone 14 to the capture zone 16. The color on the goat anti-mouse IgG($F_c$) line was read on a Minolta CR241, which can measure color from snots as small as 0.3 mm with great sensitivity and precision. Results are shown below in Table 13. The visual threshold appeared to be between 10,000 and 20,000 mIU/mL, or a relative increase of 10,000 mIU/mL over the baseline or non-visual concentration.

TABLE 13

| [hCG] (mIU/mL) | Visual | ΔE |
|---|---|---|
| 11,490 | − | 0.46 |
| 22,977 | + | 3.20 |
| 45,953 | + | 8.72 |
| 91,906 | + | 11.31 |
| 183,812 | + | 16.17 |
| 229,765 | + | 17.53 |
| 306,353 | + | 16.09 |
| 459,530 | + | 15.58 |
| 9,190,600 | + | 22.01 |

Example 13

Progesterone Assay

This assay employed a device as shown in FIG. 1 with one line of progesterone-BSA (at 3.6 mg/mL, pH 5)(BARRIER ZONE 16a) and one line of goat anti-mouse IgG ($F_c$) (affinity-purified, at 1 mg/mL) (DETECTION ZONE 16b) coated onto nitrocellulose in the capture zone 16.

Labelled anti-progesterone (0.4 μm red latex beads) was prepared analogously to the labelled HCG described earlier. It was first mixed with progesterone samples at different concentrations of progesterone: 0, 5, 10, 15, 20, 25, 30, 40 and 50 ng/mL, and then loaded onto sample pad 12 and allowed to run. The color on the goat anti-mouse IgG ($F_c$) line was read on a Minolta CR241. Results are shown in Table 14. The color on the GAMF$_c$ line became visible at progesterone concentrations above 15 ng/mL.

Table for FIG. 3

| [Progesterone] (ng/mL) | Visual | ΔE |
|---|---|---|
| 0 | − | 0.40 |
| 5 | − | 1.26 |
| 10 | − | 1.68 |
| 15 | +/− | 1.97 |
| 20 | + | 3.66 |
| 25 | + | 3.96 |
| 30 | + | 5.55 |
| 40 | + | 5.91 |
| 50 | + | 7.03 |

Example 14

PDG Assays

1. Antibody on Both Barrier and Detection Zones:

Materials and Methods:

PDG was covalently coupled to bovine immunoglobulin (BGG) at a ratio of 20:1 to 60:1. Subsequently, PDG-BGG was absorbed onto polystyrene latex beads (Bangs Laboratories, 0.4 μm) in 25 mM Tris pH 8.10 by incubating at room temperature over night on a rotator. Coated latex beads were then pelleted by centrifugation and resuspended in 1% m-BSA for blocking. Following a 4 hour incubation at room temperature on a rotator, the beads were again pelleted by centrifugation and resuspended at 1% latex in 1% m-BSA buffer. Antibody to PDG was deposited onto a 8 μm nitrocellulose membrane (S&S) at various concentrations of antibody using a X-Y-plotter. Two parallel lines of either the same or different antibodies were deposited on the same strip approximately 0.5 mm apart. One of these lines serves as the barrier zone, while the other line will be the detection zone. Following air drying, the nitrocellulose was blocked in a 1% m-BSA solution for 15 minutes and dried for 2 minutes at 45° C. in a forced air oven. The membrane was laminated and assembled into strips using a sample pad, label pad, the spotted nitrocellulose and an adsorbent pad. To assay PDG in a sample, coated latex was diluted (1/20) in BSA containing buffer. 5 μl of diluted latex were deposited at the interphase of the sample to the label pad. 35 μl sample containing various amounts of PDG diluted in urine was then added to start the test. Total time for the liquid to pass through the nitrocellulose, and the times for the appearance of the first line and the second line were recorded.

2. Antigen and Anti-species Antibody as Barrier and Detection Zones:

Materials and Methods:

PDG specific antibody was absorbed onto polystyrene latex beads (Bangs Laboratories, 0.4 μm) in 25 mM Tris pH 8.10 by incubating at room temperature over night on a rotator. Coated latex beads were then pelleted by centrifugation and resuspended in 1% m-BSA for blocking. Following a 4 hour incubation at room temperature on a rotator, the beads were again pelleted by centrifugation and resuspended at 1% latex in 1% m-BSA containing buffer. PDG conjugated to a carrier protein (BGG) was deposited onto a 8 μm nitrocellulose membrane (S&S) at various concentrations as the first zone (barrier zone) using a X-Y-plotter. A second line consisting of an antibody against the latex-bound antibody was deposited on the same strip approximately 0.5 mm apart. The second line will be the detection zone. Following air-drying, the nitrocellulose was blocked in a 1% m-BSA solution for 15 minutes and dried for 2 minutes at 45° C. in a forced air oven. The membrane was laminated and assembled into strips using a sample pad, label pad, the spotted nitrocellulose and an adsorbent pad. To assay PDG in a sample, coated latex was diluted (1/20) in BSA containing buffer. 5 μl of diluted latex were deposited at the interphase of the sample to the label pad. 35 μl sample containing various amounts of PDG diluted in urine was then added to start the test. Total time for the liquid to pass through the nitrocellulose, and the times for the appearance of the first line and the second line were recorded.

3. Antigen and Anti-species Antibody as Barrier and Detection Zones Respectively with Soluble Antibody as Competitive Capture Antibody.

Materials and Methods:

PDG specific antibody was absorbed onto polystyrene latex beads (Bangs Laboratories, 0.4 μm) in 25 mM Tris pH 8.10 by incubating at room temperature over night on a rotator. Coated latex beads were then pelleted by centrifugation and resuspended in 1% m-BSA for blocking. Following a 4 hour incubation at room temperature on a rotator, the beads were again pelleted by centrifugation and resuspended at 1% latex in 1% methylated-BSA containing buffer. PDG conjugated to a carrier protein (BGG) was deposited onto a 8 μm nitrocellulose membrane (S&S) at various concentrations as the first zone (barrier zone 16a) using a X-Y-plotter. A second line consisting of an antibody against the latex-bound antibody was deposited on the same strip approximately 0.5 mm apart. The second line will be the detection zone. Following air-drying, the nitrocellulose was blocked in a 1% m-BSA solution and then dried for 2 minutes at 45° C. in a forced air oven. The membrane was laminated and assembled into strips as in FIG. 1 using a sample pad 12, label pad 14, the spotted nitrocellulose pad 16 and an adsorbent pad 18. To assay PDG in a sample, coated latex was diluted (1/20) in BSA containing buffer. 5 μl of diluted latex beads were deposited at the interphase of the sample to the label pad. 35 μl sample containing various amounts of PDG and soluble anti-PDG antibody (25–100 μg/ml) diluted in urine was then added to start the test. The soluble antibody was either the same or a different antibody from the antibody which was bound to the latex. Total time for the liquid to pass through the nitrocellulose, and the times for the appearance of the first line and the second line were recorded.

Table 15 shows the comparison of various different clones of anti-PDG antibodies as soluble antibody. All samples were tested on strips printed with 1 mg/ml PDG-BGG (60:1) as the barrier line and 1 mg/ml Goat anti-mouse IgG on the detection zone. Latex was diluted to 0.05% prior to use. Soluble antibody was tested at 25 μg/ml and premixed with sample just prior to testing. Time (min:sec) for the detection zone to be visible is recorded below in Table 15.

TABLE 15

| PDG conc. | Ab 330 | Ab 441 | Ab 641 | Ab 642 |
|---|---|---|---|---|
| 0.0 μg/ml | neg. at 5' | neg. at 5' | neg. at 5' | neg. at 5' |
| 0.5 μg/ml | neg. at 5' | neg. at 5' | 4:38 | neg. at 5' |
| 1.0 μg/ml | 4:18 | 3:23 | 1:53 | 4:28 |
| 3.0 μg/ml | 0:47 | 0:43 | 0:30 | 0:53 |
| 5.0 μg/ml | 0:31 | 0:40 | 0:31 | 1:09 |
| 10.0 μg/ml | 0:34 | 0:28 | 0:27 | 0:33 |

Table 16 shows the comparison of different concentrations of anti-PDG antibodies clone 330 as capture antibody. All samples tested on strips printed with 1 mg/ml PDG-BGG (60:1) as the barrier line and 1 mg/ml Goat anti-mouse IgG on the detection zone. Latex was diluted to 0.05% prior to use. Soluble antibody was premixed with sample just prior to testing. Time (min:sec) for the detection zone to be visible is recorded in Table 16.

TABLE 16

| | Soluble Antibody 330 Concentration | | | |
|---|---|---|---|---|
| PDC conc. | 0.0 μg/ml | 25.0 μg/ml | 50.0 μg/ml | 100.0 μg/ml |
| 0.0 μg/ml | neg. at 5' | neg. at 5' | neg. at 5' | neg. at 5' |
| 0.5 μg/ml | 3:13 | neg. at 5' | neg. at 5' | neg. at 5' |
| 1.0 μg/ml | 1:18 | 4:18 | 3:18 | 5 min. |
| 3.0 μg/ml | 0:48 | 0:47 | 0:45 | 1:08 |
| 5.0 μg/ml | 0:35 | 0:31 | 0:29 | 0:47 |
| 10.0 μg/ml | 0:32 | 0:34 | 0:33 | 0:45 |

All publications, patents and patent applications mentioned in this specification are herein incorporated by reference into the specification to the same extent as if each individual publication, patent or patent application was specifically and individually indicated to be incorporated herein by reference.

Although the forgoing invention has been described in some detail by way of illustration and example for purposes of clarity of understanding, it will be obvious that certain changes and modifications may be practiced within the scope of the appended claims.

What is claimed is:

1. A device for determining an amount of an analyte in a sample, wherein the analyte is a member of a specific binding pair (sbp member), comprising a lateral flow matrix which defines a flow path and which comprises in series:
   a sample receiving zone;
   a labeling zone, wherein the labeling zone comprises a diffusively bound labeled first sbp member that is complementary to the analyte; and
   two or more serially oriented capture zones capable of providing visual quantitation of the amount of analyte in the sample; and wherein each capture zone comprises at least a second sbp member immobilized in the capture zone, the second sbp member being complementary to the analyte.

2. The device of claim 1, wherein the labeled first sbp member is an antibody capable of binding the analyte.

3. The device of claim 1, wherein the first sbp member includes a visually detectable label.

4. The device of claim 3, wherein the visually detectable label comprises a visible particulate label.

5. The device of claim 1, wherein the second sbp member is attached to particles and the particles are immobilized in the capture zones.

6. The device of claim 1, wherein the second sbp member is an antibody capable of binding the analyte.

7. The device of claim 1, wherein the second sbp member is labelled with a ligand and is immobilized on the capture zone by a receptor for the ligand coimmobilized on the capture zone.

8. The device of claim 7, wherein the ligand is a hapten and the receptor is a complement to the hapten.

9. The device of claim 1, wherein the second sbp member is an antibody against a complex formed between the analyte and the first sbp member.

10. The device of claim 1, wherein the analyte is a polyepitopic molecule and the first and second sbp members are antibodies against different epitopes of the analyte.

11. The device of claim 1, wherein the analyte is human IgE.

12. The device of claim 1, wherein the first sbp member is goat anti-human IgE and the second sbp member is mouse monoclonal anti-human IgE.

13. The device of claim 1, wherein the lateral flow matrix comprises two capture zones having the second sbp member uniformly immobilized in the single capture zones.

14. The device of claim 1, wherein the sample receiving zone comprises an amount of a third sbp member immobilized within the sample receiving zone and complementary to the analyte, the amount being sufficient to bind a threshold level of the analyte.

15. The device of claim 1, wherein the device comprises a plurality of discrete lateral flow matrices.

16. The device of claim 15, wherein the plurality of discrete lateral flow matrices have a common sample receiving zone, whereby a sample deposited in the sample receiving zone flows along each of the lateral flow matrices.

17. The device of claim 1 wherein a predetermined amount of the second sbp member is present in each capture zone.

18. A device for determining an amount of an analyte in a sample, wherein the analyte is a member of a specific binding pair (sbp member), comprising a lateral flow matrix which defines a flow path and which comprises in series:
a sample receiving zone;
a labeling zone, wherein the labeling zone comprises a diffusively bound labeled first sbp member that is complementary to the analyte; and
two or more serially oriented capture zones capable of providing visual quantitation of the amount of analyte in the sample; wherein each capture zone comprises at least a second sbp member immobilized in the capture zone, the second sbp member being complementary to the analyte, and wherein the lateral flow matrix comprises a plurality of spatially separated capture zones.

19. The device of claim 18 wherein a predetermined amount of the second sbp member is present in each capture zone.

20. A device for determining an amount of an analyte in a sample, wherein the analyte is a member of a specific binding pair (sbp member), comprising a lateral flow matrix which defines a flow path and which comprises in series:
a sample receiving zone;
a labeling zone, wherein the labeling zone comprises a diffusively bound labeled first sbp member that is complementary to the analyte;
two or more serially oriented capture zones capable of providing visual quantitation of the amount of analyte in the sample; and wherein each capture zone comprises at least a second sbp member immobilized in the capture zone, the second sbp member being complementary to the analyte; and
wherein the pattern of binding of labeled analyte within the capture zone is a function of the analyte concentration.

21. The device of claim 20 wherein a predetermined amount of the second sbp member is present in each capture zone.

* * * * *